(12) United States Patent
Riddell et al.

(10) Patent No.: US 10,400,215 B2
(45) Date of Patent: Sep. 3, 2019

(54) ADOPTIVE TRANSFER OF CD8+ T CELL CLONES DERIVED FROM CENTRAL MEMORY CELLS

(71) Applicants: City of Hope, Duarte, CA (US); Fred Hutchinson Cancer Research Center, Seattle, WA (US)

(72) Inventors: Stanley R. Riddell, Sammamish, WA (US); Susanna Carolina Berger, Seattle, WA (US); Michael C. Jensen, Bainbridge Island, WA (US)

(73) Assignees: City of Home, Duarte, CA (US); Fred Hutchinson Cancer Research Center, Seattle, WA (US)

( * ) Notice: Subject to any disclaimer, the term of this patent is extended or adjusted under 35 U.S.C. 154(b) by 465 days.

(21) Appl. No.: 14/303,385

(22) Filed: Jun. 12, 2014

(65) Prior Publication Data
US 2014/0356398 A1    Dec. 4, 2014

Related U.S. Application Data

(63) Continuation of application No. 11/870,776, filed on Oct. 11, 2007, now abandoned.

(60) Provisional application No. 60/867,880, filed on Nov. 30, 2006.

(51) Int. Cl.
| *C12N 5/0783* | (2010.01) |
| *A61K 35/17* | (2015.01) |
| *C12N 15/85* | (2006.01) |
| *A61K 39/00* | (2006.01) |

(52) U.S. Cl.
CPC ............ *C12N 5/0638* (2013.01); *A61K 35/17* (2013.01); *C12N 5/0636* (2013.01); *C12N 15/85* (2013.01); *A61K 39/0011* (2013.01); *A61K 2039/5158* (2013.01); *C12N 2501/2315* (2013.01)

(58) Field of Classification Search
None
See application file for complete search history.

(56) References Cited

U.S. PATENT DOCUMENTS

| 4,690,915 A | 9/1987 | Rosenberg |
| 5,399,346 A | 3/1995 | Anderson et al. |
| 5,827,642 A | 10/1998 | Riddell et al. |
| 6,040,177 A | 3/2000 | Riddell et al. |
| 6,316,257 B1 | 11/2001 | Flyer et al. |
| 6,344,192 B1 | 2/2002 | Grooten et al. |
| 6,451,316 B1 | 9/2002 | Srivastava |
| 6,805,861 B2 | 10/2004 | Stauss |
| 6,890,753 B2 | 5/2005 | Flyer et al. |
| RE39,788 E | 8/2007 | Anderson et al. |
| 2003/0026790 A1 | 2/2003 | Hwu et al. |
| 2003/0170238 A1 | 9/2003 | Gruenberg et al. |
| 2005/0129671 A1 | 6/2005 | Cooper et al. |
| 2006/0121005 A1 | 6/2006 | Berenson et al. |

FOREIGN PATENT DOCUMENTS

| WO | 2005/045009 A1 | 5/2005 | |
| WO | WO-2006065495 A2 * | 6/2006 | .......... C12N 5/0636 |
| WO | 2008/066609 A1 | 6/2008 | |

OTHER PUBLICATIONS

Peng et al. (Microbes and Infection 8 (2006) 2424-2431).*
Oh et al., Retrovirology, (2006) vol. 3, No. Suppl.1, pp. S17, International Meeting of the Institute-of-Human-Virology. Baltimore, MD, USA. Nov. 17-21, 2006.*
Villinger et al., Vaccine 22 (2004) 3510-3521.*
Sallusto et al., Nat Med. Oct. 11, 2011;17(10):1182-3 (Year: 2011).*
Yu et al., Nat Med. Dec. 2005;11(12):1282-3 (Year: 2005).*
Prabhu et al. (PLoS One 11(9): e0162242, pp. 1-17 and supporting information pp. 18-24). (Year: 2016).*
Bisset et al. (Eur J Haematol 2004: 72: 203-212). (Year: 2004).*
Dudley et al., Nature Review Cancer, 2003, vol. 3, pp. 666-675. (Year: 2003).*
Mortarini et al. (Cancer Research 63, 2535-2545, 2003). (Year: 2003).*
Wang et al. (Journal of Translational Medicine 2004). (Year: 2004).*
Liu et al. (J Immunother 2006;29:284-293). (Year: 2006).*
Wolfl et al. (Cancer Immunol Immunother (2011) 60:173-186). (Year: 2011).*
Zeng et al., "Synergy of IL-21 and IL-15 in regulating CD8+ T cell expansion and function," *JEM* 201(1):139-148 (Jan. 3, 2005).
Appay et al., "Memory CD8+ T cells vary in differentiation phenotype in different persistent virus infections," *Nature Medicine* 8(4):379-385 (2002).
Baron et al., "The Repertoires of Circulating Human CD8+ Central and Effector Memory T Cell Subsets Are Largely Distinct," *Immunity* 18:193-204 (2003).
Barratt-Boyes et al., "Maturation and Trafficking of Monocyte Derived Dendritic Cells in Monkeys: Implications for Dendritic Cell-Based Vaccines," *The Journal of Immunology* 164:2487-2495 (2000).
Becker et al., "Interleukin 15 Is Required for Proliferative Renewal of Virus-Specific Memory CD8 T Cells," *J. Exp. Med.* 195(12):1541-1548 (2002).

(Continued)

*Primary Examiner* — Zachary S Skelding
(74) *Attorney, Agent, or Firm* — Seed IP Law Group LLP

(57) ABSTRACT

The present invention provides a method of carrying out adoptive immunotherapy in a primate subject in need thereof by administering the subject a cytotoxic T lymphocytes (CTL) preparation in a treatment-effective amount. The method comprises administering as the CTL preparation a preparation consisting essentially of an in vitro expanded primate CTL population, the CTL population enriched prior to expansion for central memory T lymphocytes, and depleted prior to expansion of effector memory T lymphocytes. In some embodiments, the method may further comprise concurrently administering Interleukin-15 to the subject in an amount effective to increase the proliferation of the central memory T cells in the subject. Pharmaceutical formulations produced by the method, and methods of using the same, are also described.

16 Claims, 24 Drawing Sheets

(56) References Cited

OTHER PUBLICATIONS

Berger et al., "Nonmyeloablative Immunosuppressive Regimen Prolongs In Vivo Persistence of Gene-Modified Autologous T Cells in a Nonhuman Primate Model," *Journal of Virology* 75(2):799-808 (2001).
Berger et al., "Pharmacologically regulated Fas-mediated death of adoptively transferred T cells in a nonhuman primate model," *Blood* 103(4):1261-1269 (2004).
Berger et al., "Analysis of transgene-specific immune responses that limit the in vivo persistence of adoptively transferred HSV-TK-modified donor T cells after allogeneic hematopoietic cell transplantation," *Blood* 107(6):2294-2302 (2006).
Berger et al., "Adoptive transfer of effector $CD8^+$ T cells derived from central memory cells establishes persistent T cell memory in primates," *J. Clin. Invest.* doi:10.1172/JC132103 (8 pages) (2007).
Blattman et al., "Cancer Immunotherapy: A Treatment for the Masses," *Science* 305:200-205 (2004).
Bleakley et al., "Molecules and Mechanisms of the Graft-Versus-Leukaemia Effect," *Nature Reviews—Cancer* 4:371-380 (2004).
Bollard et al., "Cytotoxic T Lymphocyte Therapy for Epstein-Barr Virus+ Hodgkin's Disease," *J. Exp. Med.* 200(12):1623-1633 (2004).
Brentjens et al., "Eradication of systemic B-cell tumors by genetically targeted human T lymphocytes co-stimulated by CD80 and interleukin-15," *Nature Medicine* 9(3):279-286 (2003).
Butcher et al., "Lymphocyte Homing and Homeostasis," *Science* 272:60-66 (1996).
Chao et al., "Mechanisms of L-Selectin Regulation by Activated T Cells," *The Journal of Immunology* 159(4):1686-1694 (1997).
Cooper et al., "Manufacturing of gene-modified cytotoxic T lymphocytes for autologous cellular therapy for lymphoma," *Cytotherapy* 8(2):105-117 (2006).
Cui et al., "Generation of effector $CD8^+$ T cells and their conversion to memory T cells," *Immunological Reviews* 236:151-166 (2010).
Distler et al., "Rapid expansion of myeloid leukemia-reactive cytotoxic T cells from $CD8(+)CD62L(+)$ blood lymphocytes of HLA-matched healthy donors in vitro," *Blood* 108(11) Part 1, pp. 924A (2006).
Dudley et al., "Adoptive Transfer of Cloned Melanoma-Reactive T Lymphocytes for the Treatment of Patients with Metastatic Melanoma," *Journal of Immunotherapy* 24(4):363-373 (2001).
Dudley et al., "A Phase I Study of Nonmyeloablative Chemotherapy and Adoptive Transfer of Autologous Tumor Antigen-Specific T Lymphocytes in Patients with Metastatic Melanoma," *J. Immunother.* 25(3):243-251 (2002).
Dudley et al., "Cancer Regression and Autoimmunity in Patients After Clonal Repopulation with Antitumor Lymphocytes," *Science* 298(5594):850-854 (2002).
Dudley et al., "Adoptive Cell Transfer Therapy Following Non-Myeloablative but Lymphodepleting Chemotherapy for the Treatment of Patients with Refractory Metastatic Melanoma," *J. Clin. Oncol.* 23(10):2346-2357 (2005).
Fearon et al., "Arrested differentiation, the self-renewing memory lymphocyte, and vaccination," *Science* 293:248-250 (2001).
Gattinoni et al., "Adoptive immunotherapy for cancer: building on success," *Nature Reviews Immunology* 6:383-393 (2006).
Gattinoni et al., "Removal of homeostatic cytokine sinks by lymphodepletion enhances the efficacy of adoptively transferred tumor-specific $CD8^+$ cells," *Journal of Experimental Medicine* 202(7):907-912 (2005).
Gattinoni et al., "Acquisition of full effector function in vitro paradoxically impairs the in vivo antitumor efficacy of adoptively transferred CD8+ T cells," *The Journal of Clinical Investigation* 118(6):1616-1626 (2005).
Hinrichs et al., "Programming CD8+ T cells for effective immunotherapy," *Curr Opin Immunol.* 18(3):363-370 (2006).
Kaech et al., "Selective expression of the interleukin 7 receptor identifies effector CD8 T cells that give rise to long-lived memory cells," *Nature Immunology* 4(12):1191-1198 (2003).
Kessels et al., "Immunotherapy through TCR gene transfer," *Nature Immunology* 2(10):957-961 (2001).
Klebanoff et al., "IL-15 enhances the in vivo antitumor activity of tumor reactive $CD8^+$ T Cells," *PNAS* 101(7):1969-1974 (2004).
Klebanoff et al., "Central memory self/tumor-reactive CD8* T cells confer superior antitumor immunity compared with effector memory T cells," *PNAS* 102(27):9571-9576 (2005).
Klebanoff et al., "$CD8^+$ T-cell memory in tumor immunology and immunotherapy," *Immunological Reviews* 211:214-224 (2006).
Lanzavecchia et al., "Understanding the generation and function of memory T cell subsets," *Current Opinion in Immunology* 17:326-332 (2005).
Lee et al., "Characterization of circulating T cells specific for tumor-associated antigens in melanoma patients," *Nature Medicine* 5(6):677-685 (1999).
Leffrancois et al., "The descent of memory T-cell subsets," *Nat. Rev. Immunol.* 6:618-623 (2006).
Liu et al., "IL-15 mimics T cell receptor crosslinking in the induction of cellular proliferation, gene expression, and cytotoxicity in $CD8^+$ memory T cells," *PNAS* 99(9):6192-6197 (2002).
Marzo et al., "Initial T cell frequency dictates memory $CD8^+$ T cell lineage commitment," *Nat. Immunol.* 6(8):793-799 (2005).
Masopust et al., "The role of programming in memory T-cell development," *Current Opinion in Immunology* 16:217-225 (2004).
Meidenbauer et al., "Survival and Tumor Localization of Adoptively Transferred Melan-A-Specific T Cells in Melanoma Patients," *The Journal of Immunology* 170:2161-2169 (2003).
Miyahara et al., "Effector $CD8^+$ T cells mediate inflammation and airway hyper-responsiveness," *Nature Medicine* 10(8):865-869 (2004).
Morecki et al., "Retrivirus-mediated gene transfer into CD4± and CD8± human T cell subsets derived from tumor-infiltrating lymphocytes and peripheral blood mononuclear cells," *Cancer Immunol Immunother* 32:342-352 (1991).
Morgan et al., "Cancer Regression in Patients After Transfer of Genetically Engineered Lymphocytes," *Science* 314:126-129 (2006).
Ochsenbein et al., "CD27 Expression Promoates Long-Term Survival of Functional Effector-Memory CD8+ Cytotox T Lymphocytes in HIV-infected Patients," *J. Exp. Med.* 200(11):1407-1417 (2004).
Overwijk et al., "Tumor Regression and Autoimmunity after Reversal of a Functionally Tolerant State of Self-reactive $CD8^+$ T Cells," *The Journal of Experimental Medicine* 198(4):569-580 (2003).
Pahl-Seibert et al., "Highly Protective In Vivo Function of Cytomegalovirus IE1 Epitope-Specific Memory CD8 T Cells Purified by T-Cell Receptor-Based Cell Sorting," *Journal of Virology* 79(9):5400-5413 (2005).
Riddell et al., "The use of anti-CD3 and anti-CD28 monoclonal antibodies to clone and expand human antigen-specific T Cells," *Journal of Immunological Methods* 128:189-201 (1990).
Riddell et al., "Restoration of Viral Immunity in Immunodeficient Humans by the Adoptive Transfer of T Cell Clones," *Science* 257:238-241 (1992).
Riddell et al., "T-cell mediated rejection of gene-modified HIV-specific cytotoxic T lymphocytes in HIV-infected patients," *Nature Medicine* 2(2):216-223 (1996).
Rivoltini et al., "Immunity to cancer: attack and escape in T lymphocyte-tumor cell interaction," *Immunological Reviews* 188:97-113 (2002).
Robins et al., "Comprehensive assessment of T-cell receptor β-chain diversity in αβ T Cells," *Blood* 114(19):4099-4107 (2009).
Rooney et al., "Infusion of Cytotoxic T Cells for the Prevention and Treatment of Epstein-Barr Virus-Induced Lymphoma in Allogeneic Transplant Recipients," *Blood* 92(5):1549-1555 (1998).
Roszkowski et al., "Simultaneous Generation of $CD8^+$ and $CD4^+$ Melanoma-Reactive T Cells by Retroviral-Mediated Transfer of a Single T-Cell Receptor," *Cancer Res.* 65(4):1570-1576 (2005).
Sadelain et al., "Targeting Tumours with Genetically Enhanced T Lymphocytes," *Nature Reviews—Cancer* 3:35-45 (2003).
Sallusto et al., "Two subsets of memory T lymphocytes with distinct homing potentials and effector functions," *Nature* 401(6754):708-712 (1999).
Sallusto et al., "Central Memory and Effector Memory T Cell Subsets: Function, Generation, and Maintenance," *Annu. Rev. Immunol.* 22:745-763 (2004).

(56) References Cited

OTHER PUBLICATIONS

Schluns et al., "Cutting Edge: Requirement for IL-15 in the Generation of Primary and Memory Antigen-Specific CD8 T Cells," *The Journal of Immunology* 168:4827-4831 (2002).
Till et al., "Adoptive immunotherapy for indolent non-Hodgkin's lymphoma and mantle cell lymphoma using genetically modified autologous CD20-specific T cells," *Blood* 112(6):2261-2271 (2008).
Topp et al., "Restoration of CD28 Expression in CD82− CD8+ Memory Effector of T Cells Reconstitutes Antigen-induced IL-2 Production," *J. Exp. Med.* 198(6):947-955 (2003).
Turtle et al., "A Distinct Subset of Self-Renewing Human Memory CD8+ T Cells Survives Cytotoxic Chemotherapy," *Immunity* 31:1-11 (2009).
Van De Griend et al., "Rapid Expansion of Human Cytotoxic T Cell Clones: Growth Promotion by a Heat-Labile Serum Component and by Various Types of Feeder Cells," *Journal of Immunological Method* 66:285-298 (1984).
Van De Griend et al., "Rapid Expansion of Allospecific Cytotoxic T Cell Clones Using Nonspecific Feeder Cell Lines Without Further Addition of Exogenous IL2," *Transplantation* 38(4):401-406 (1984).
Walter et al., "Reconstitution of Cellular Immunity Against Cytomegalovirus in Recipients of Allogeneic Bone Marrow by Transfer of T-Cell Clones From the Donor," *The New England Journal of Medicine* 333:1038-1044 (1995).
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725 (2007).
Wang et al., "Cellular Immunotherapy for Follicular Lymphoma Using Genetically Modified CD20-Specific CD8+ Cytotoxic T Lymphocytes," *Molecular Therapy* 9(4):577-586 (2004).
Warren et al., "T-cell therapy targeting histocompatibility Ags for the treatment of leukemia and renal-cell carcinoma," *Cytotherapy* 4(5):441-441 (2002).
Wherry et al., "Lineage relationship and protective immunity of memory CD8 T cell subsets," *Nature Immunology* 4(3):225-234 (2003).
Willinger et al., "Molecular Signatures Distinguish Human Central Memory from Effector Memory CD8 T Cell Subsets," *The Journal of Immunology* 175:5895-5903 (2005).
Yee et al., "Melanocyte Destruction After Antigen-specific Immunotherapy of Melanoma: Direct Evidence of T Cell-mediated Vitiligo," *J. Exp. Med.* 192(11):1637-1643 (2000).
Yee et al., "Adoptive T cell therapy using antigen-specific CD8+ T cell clones for the treatment of patients with metastatic melanoma: In vivo persistence, migration, and antitumor effect of transferred T cells," *PNAS* 99(25):16168-16173 (2002).
Youngblood et al., "Making memories that last a lifetime: heritable functions of self-renewing memory CD8 T cells," *International Immunology* 22(10):797-803 (2010).
Nelson et al., "Cytoplasmic domains of the interleukin-2 receptor $\beta$ and $\gamma$ chains mediate the signal for T-cell proliferation," *Nature* 369:333-336 (May 26, 1994).

\* cited by examiner

ADOPTIVE TRANSFER OF CD8+ T CELL CLONES DERIVED FROM CENTRAL MEMORY CELLS

CROSS-REFERENCES TO RELATED APPLICATIONS

This application is a continuation of co-pending U.S. patent application Ser. No. 11/870,776, filed Oct. 11, 2007, which claims priority to U.S. Provisional Application No. 60/867,880, filed Nov. 30, 2006. The disclosures of these applications are incorporated herein by reference in their entireties.

STATEMENT OF GOVERNMENT INTEREST

This invention was made with government support under CA114536 awarded by the National Institutes of Health. The government has certain rights to the invention.

FIELD OF THE INVENTION

The present invention concerns methods and compositions for carrying out adoptive immunotherapy.

BACKGROUND OF THE INVENTION

Studies in rodents have demonstrated that adoptive immunotherapy with antigen specific T cells is effective for cancer and infections, and there is evidence this modality has therapeutic activity in humans[1-8]. For clinical applications, it is necessary to isolate T cells of a desired antigen specificity or to engineer T cells to express receptors that target infected or transformed cells, and then expand these cells in culture[9-14]. The transfer of T cell clones is appealing because it enables control of specificity and function, and facilitates evaluation of in vivo persistence, toxicity and efficacy. Additionally, in the setting of allogeneic stem cell transplantation, the administration to recipients of T cell clones from the donor that target pathogens or malignant cells can avoid graft-versus-host disease that occurs with infusion of unselected donor T cells[3,4,15]. However, it is apparent from clinical studies that the efficacy of cultured T cells, particularly cloned CD8+ T cells, is frequently limited by their failure to persist after adoptive transfer[16,17].

The pool of lymphocytes from which CD8+ T cells for adoptive immunotherapy can be derived contains naïve and long-lived, antigen experienced memory T cells ($T_M$). $T_M$ can be divided further into subsets of central memory ($T_{CM}$) and effector memory ($T_{EM}$) cells that differ in phenotype, homing properties and function's. CD8+ $T_{CM}$ express CD62L and CCR7, which promote migration into lymph nodes, and proliferate rapidly if re-exposed to antigen. CD8+ $T_{EM}$ lack CD62L enabling migration to peripheral tissues, and exhibit immediate effector function[19].

In response to antigen stimulation, CD8+ $T_{CM}$ and $T_{EM}$ both differentiate into cytolytic effector T cells ($T_E$) that express a high level of granzymes and perforin, but are short-lived[20]. Thus, the poor survival of T cells in clinical immunotherapy trials may simply result from their differentiation during in vitro culture to $T_E$ that are destined to die[17,21,22].

SUMMARY OF THE INVENTION

A first aspect of the present invention is a method of carrying out adoptive immunotherapy in a primate subject in need thereof by administering the subject a cytotoxic T lymphocytes (CTL) preparation in a treatment-effective amount. The method comprises administering as the CTL preparation a preparation consisting essentially of an in vitro expanded (e.g., grown in vitro for 1, 2, or 3 days up to 3 or 4 weeks or more) primate CTL population, the CTL population enriched prior to expansion for central memory T lymphocytes, and depleted prior to expansion of effector memory T lymphocytes. In some embodiments, the method may further comprise concurrently administering Interleukin-15 to the subject in an amount effective to increase the proliferation of the central memory T cells in the subject.

A further aspect of the invention is a pharmaceutical formulation comprising, consisting essentially of or consisting of an in vitro expanded primate cytotoxic T lymphocyte (CTL) population, the CTL population enriched prior to expansion for central memory T lymphocytes, and depleted prior to expansion of effector memory T lymphocytes.

A further aspect of the invention is the use of a formulation as described herein for the preparation of a medicament for carrying out a method as described herein (e.g., treating cancer or an infectious disease in a human, or primate, subject).

In some embodiments the CTL preparation (or population) is produced by the process of: (a) collecting a first CTL population from a donor; (b) separating a CTL subpopulation enriched for CD62L+ central memory T lymphocytes and depleted of CD62L− effector memory T lymphocytes to produce a central memory-enriched CTL subpopulation; (c) expanding the central memory-enriched CTL subpopulation in vitro in a culture medium (e.g., for 1, 2, or 3 days up to 3 or 4 weeks or more); and then (d) collecting cells from the culture medium to produce the CTL preparation. The separating step "b" can in some embodiments be carried out by: (i) contacting the first CTL population to anti-CD62L antibody, wherein the antibody is immobilized on a solid support, so that central memory cells bind to the support; then (ii) separating the support from the CTL population with central memory cells bound thereto; (iii) and then separating the central memory cells from the solid support to produce the central memory enriched CTL subpopulation. In some embodiments, the expanding step "c" further comprises administering Interleukin-15 to the central memory subpopulation in vitro.

In some embodiments, the central memory-enriched T cells are modified in vitro with at least one gene that targets (e.g., specifically binds to) cancer cells or other pathogenic cells in the subject.

BRIEF DESCRIPTION OF THE DRAWINGS

FIG. 1a. CMV IE-specific memory T cells are present in both CD62L+ and CD62L− subsets of CD8+ peripheral blood lymphocytes. PBMC were sorted into CD62L−CD8+ and CD62L+CD8+ fractions after staining with anti-CD8 and anti-CD62L antibodies (upper panels). The CD62L− and CD62L+ fractions were stimulated for 6 hours with autologous CD40L− activated B cells pulsed with medium alone or with CMV-IE peptide. Brefeldin A was added for the final 4 hours and CD8+ T cells that produced IFN-γ were detected by staining for intracellular INF-γ. The lower left panels show INF-γ production by the CD62L−CD8+ subset and the lower right panels show IFN-γ production by the CD62L−

CD8+ subset. Data from macaque 02269 is shown and is representative of data obtained in four consecutive macaques.

Figure 1A:
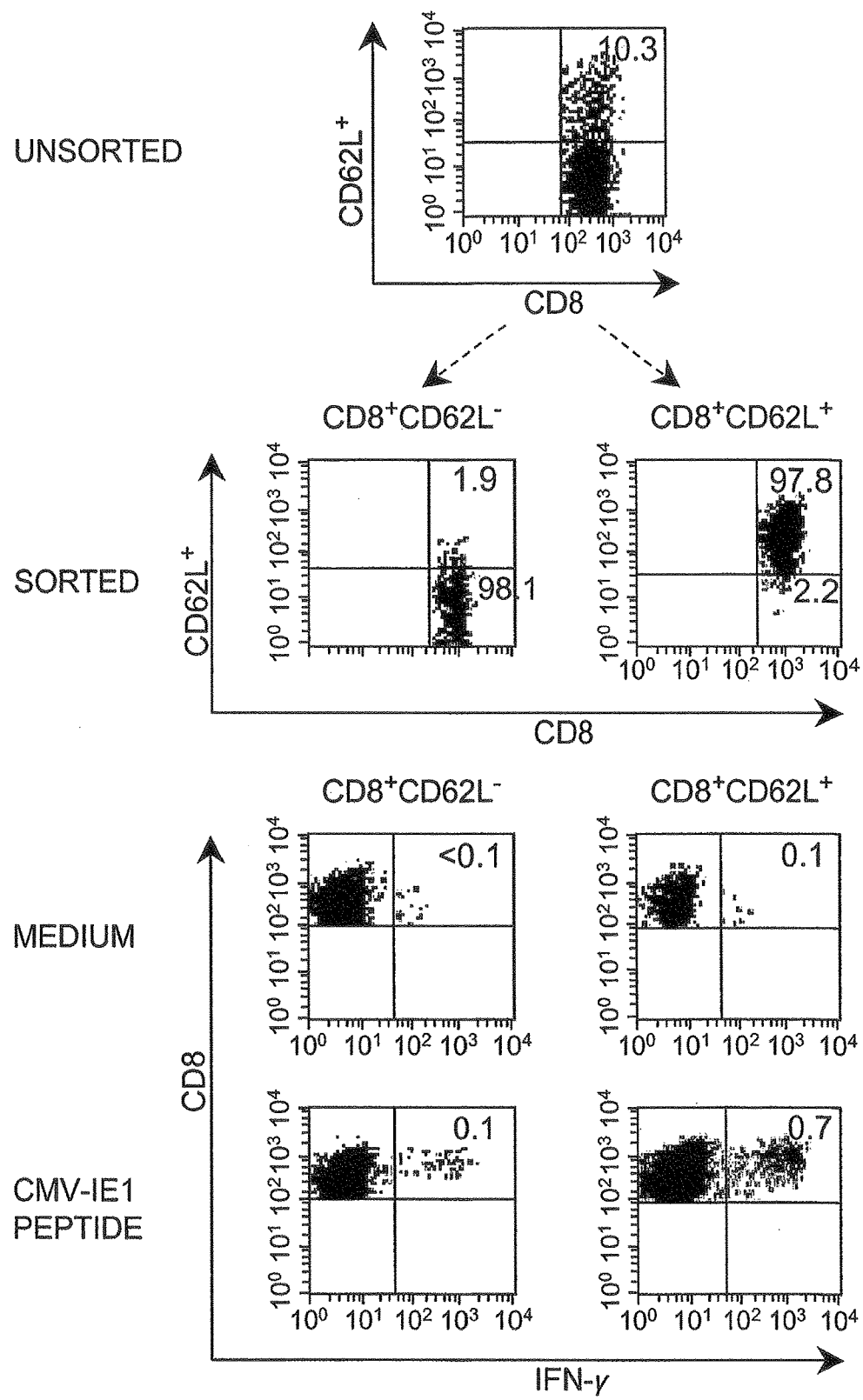
FIGS. 1a-1d show isolation and genetic modification of CMV-specific CD8+ T cell clones from CD62L− and CD62L+ T cell subsets for adoptive transfer.
Figure 1B:
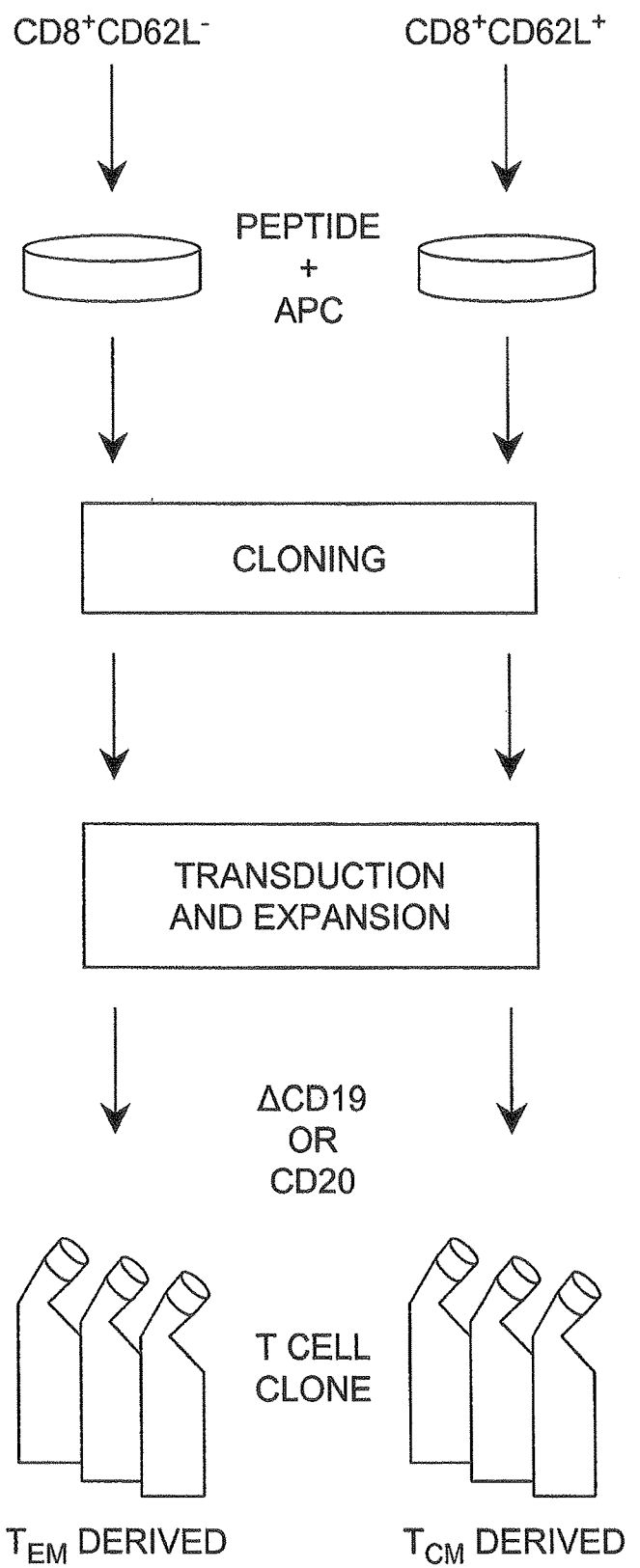

FIG. 1b. Strategy for the isolation of CMV-specific CD8+ T cell clones from CD62L− $T_{EM}$ and CD62L+ $T_{CM}$ subsets. Aliquots of PBMC were obtained from each macaque and sorted into CD62L−CD8+ and CD62L+CD8+ fractions after staining with anti-CD8 and anti-CD62L antibodies. The sorted T cells were cultured with autologous monocytes pulsed with the CMV IE peptide and after 1 week of stimulation, T cells from the cultures were cloned by limiting dilution. T cell clones were screened to identify those that lysed autologous peptide-pulsed target cells, and then transduced with a retroviral vector that encoded a cell surface ΔCD19 or CD20 molecule. Individual T cell clones were expanded in vitro to >5×10$^9$ cells by stimulation with anti-CD3 and anti-CD28 antibodies in cultures supplemented with γ-irradiated human PBMC and EBV-LCL prior to adoptive transfer.

Figure 1C:
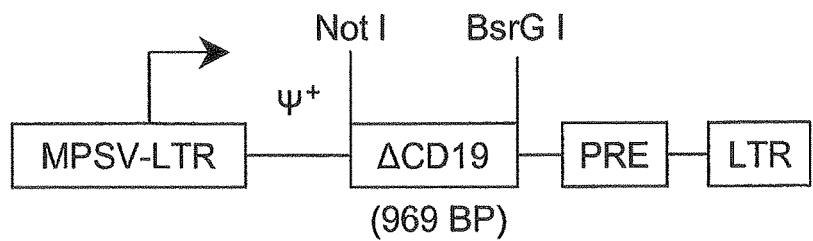
Figure 1C:
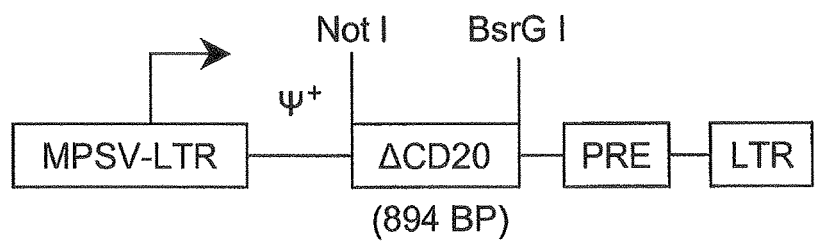

FIG. 1c. Retroviral vector constructs encoding for macaque cell surface marker genes. Abbreviations: MPSV-LTR, myeloproliferative sarcoma virus retroviral long terminal repeat; ψ+, extended packaging signal; PRE, woodchuck hepatitis virus posttranscriptional regulatory element; ΔCD19, truncated macaque CD19 cDNA encoding the extracellular and transmembrane domains, and 4 aa of the cytosolic tail; CD20, full-length macaque CD20 cDNA.

Figure 1D:
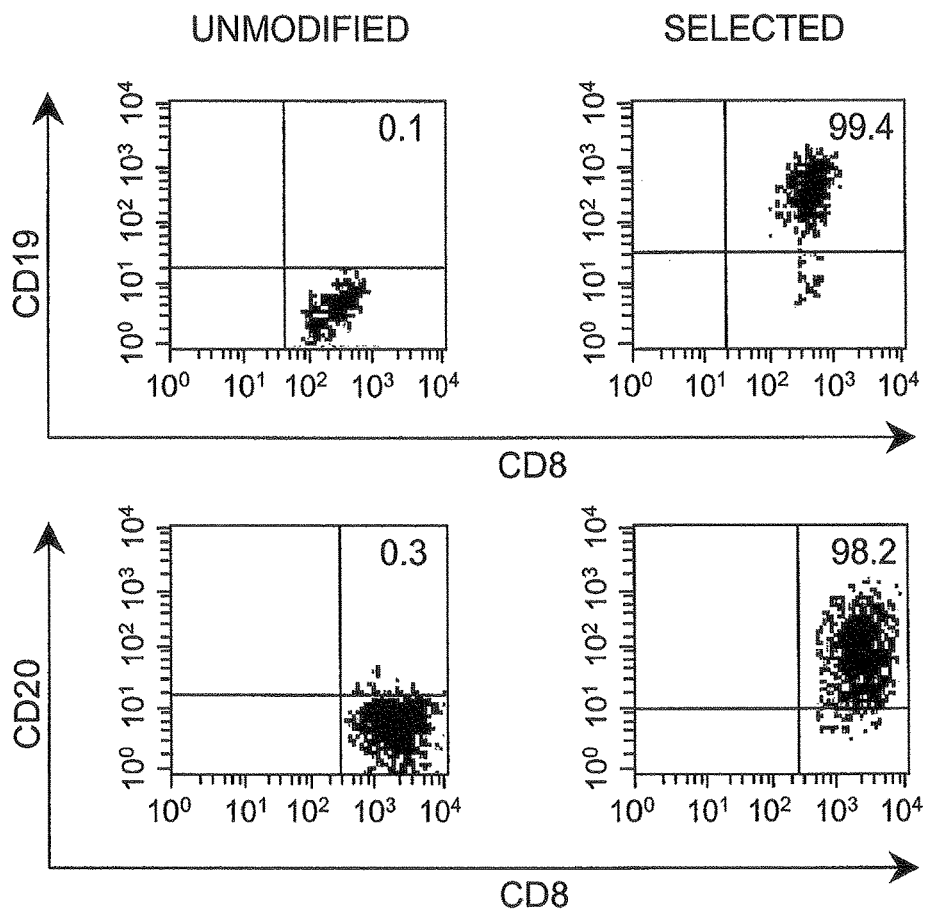

FIG. 1d. Immunomagnetic bead selection of ΔCD19 and CD20-modified CD8+ T cell clones. Transduced T cells were enriched for ΔCD19 or CD20 expressing cells on day 8 after transduction using a two-step immunomagnetic selection with anti-CD 19 or anti-CD20 antibodies and rat anti-mouse IgG coupled microbeads. Aliquots of unmodified (left panels) and ΔCD19 or CD20-modified T cells (right panels) were removed after selection, co-stained with anti-CD8 and anti-CD 19 or anti-CD20 antibodies, and analyzed by flow cytometry to assess purity. The percentages of CD8+ T cells positive for the transgene are indicated.

FIGS. 2a-2d show CMV-specific CD8+ T cell clones derived from $T_{CM}$ and $T_{EM}$ subsets exhibit an effector phenotype, and comparable avidity and proliferation in vitro.

Figure 2A:
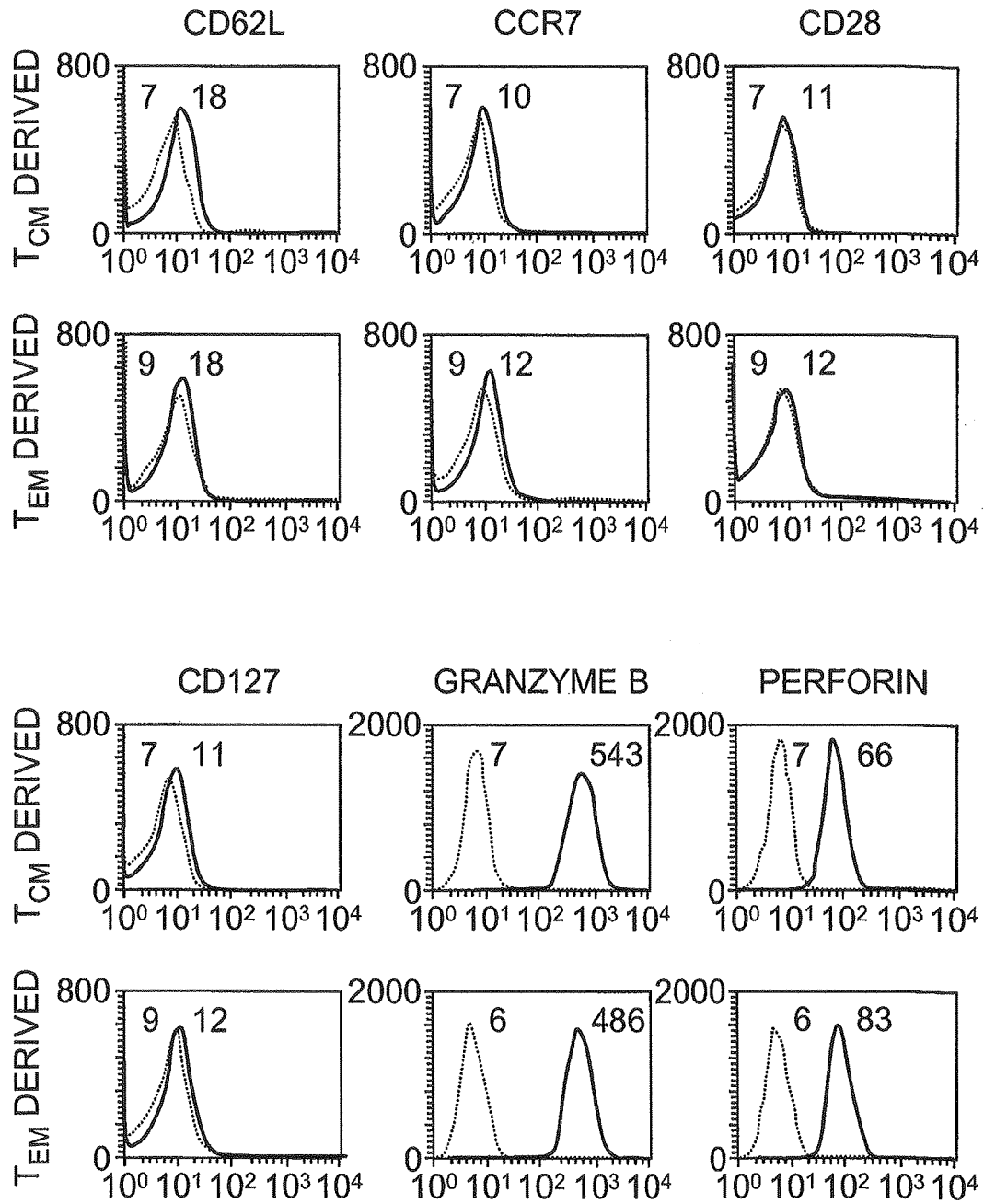

FIG. 2a. Individual $T_{CM}$ and $T_{EM}$-derived macaque CMV-specific CD8+ T cell clones were examined by flow cytometry for expression of CD62L, CCR7, CD28, CD127, granzyme B and perforin (bold line) and stained with isotype control antibodies (dotted line). Inset values represent the mean fluorescence intensity (MFI). The data is shown for T cell clones that were adoptively transferred to macaque 02269 and is representative of the data for all of the T cell clones used in adoptive transfer experiments in the three macaques.

Figure 2B:
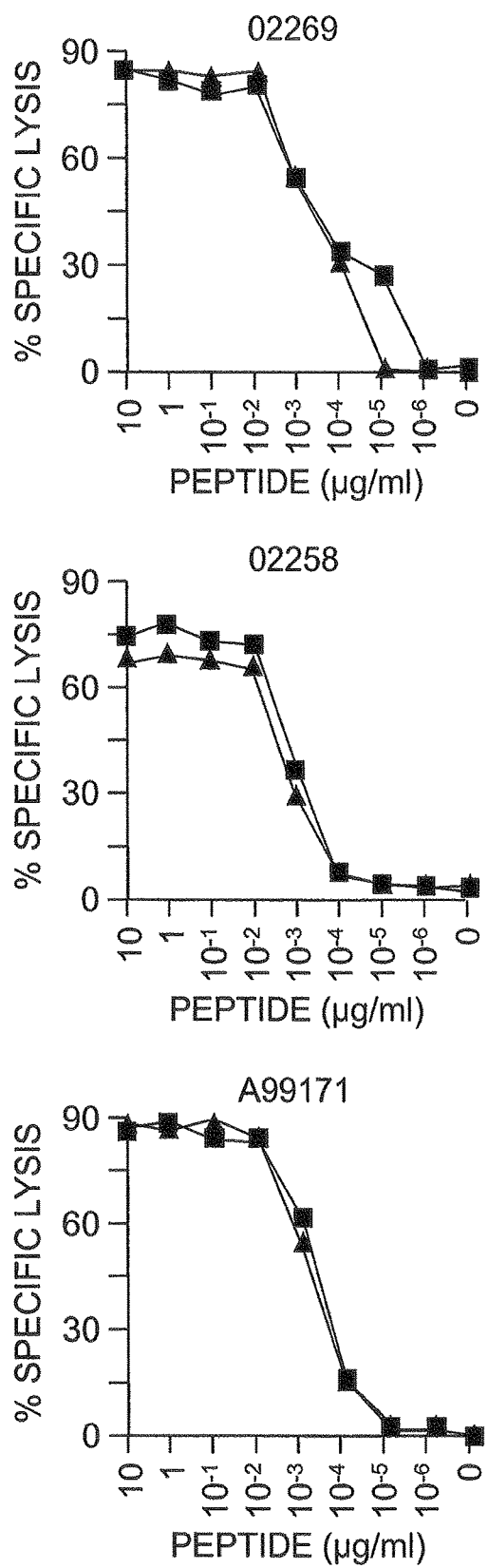

FIG. 2b. Cytotoxic activity of each pair of $T_{EM}$ (filled triangle) and $T_{CM}$ (filled square)-derived CMV-specific CD8+ T cell clones used in adoptive transfer was examined in a 4-hour chromium release assay at an effector to target ratio of 20:1 using autologous target cells pulsed with the CMV IE peptide at various concentrations. The sequences of the IE-1 peptides were KKGDIKDRV (02269) and EEHVKLFFK (A99171), the sequence of the IE-2 peptide was ATTRSLEYK (02258).

Figure 2C:
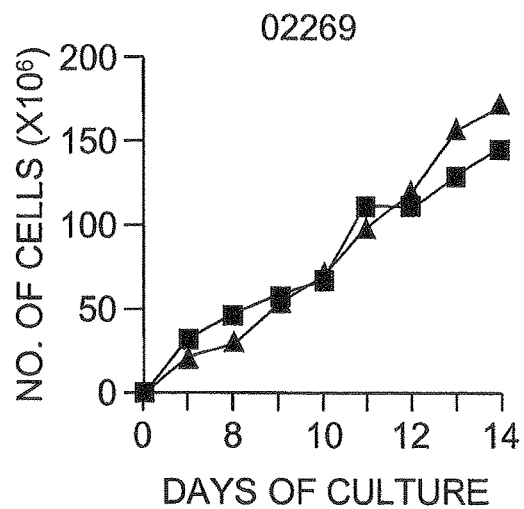
Figure 2C:
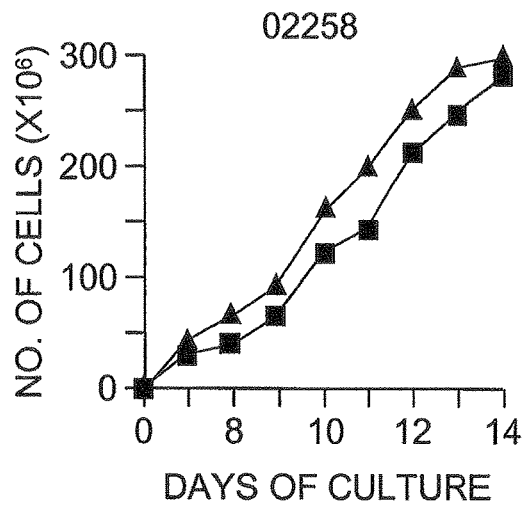
Figure 2C:
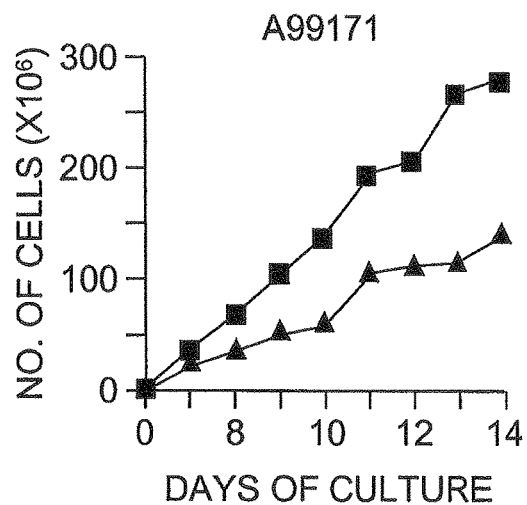

FIG. 2c. In vitro growth of CMV-specific CD8+ T cell clones. The $T_{EM}$ (filled triangle) and $T_{CM}$ (filled square) derived T cell clones used for adoptive transfer were stimulated with anti-CD3 and anti-CD28 in the presence of γ-irradiated feeder cells and IL-2 (50 U/ml). Cell growth over 14 days of culture was measured by counting viable cells using trypan blue exclusion.

Figure 2D:
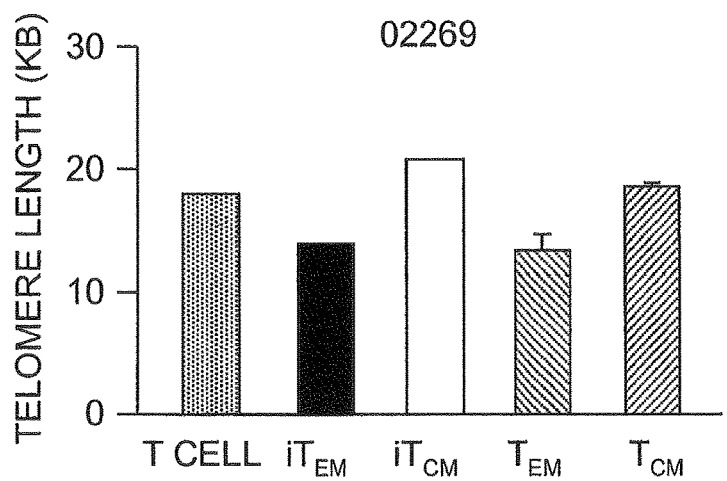
Figure 2D:
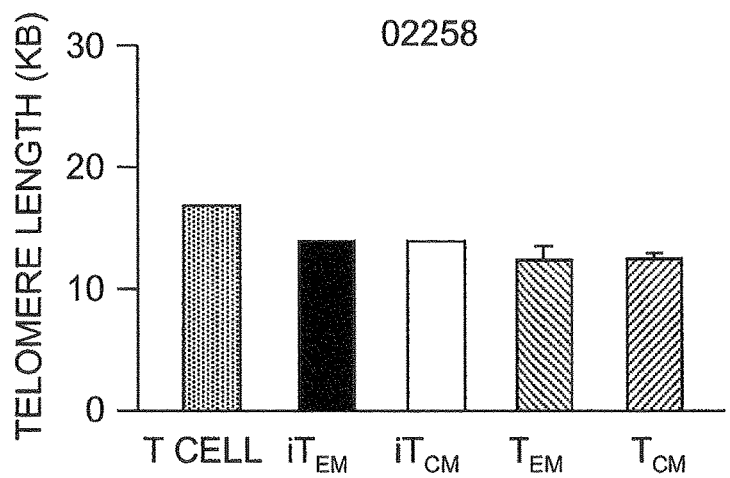
Figure 2D:
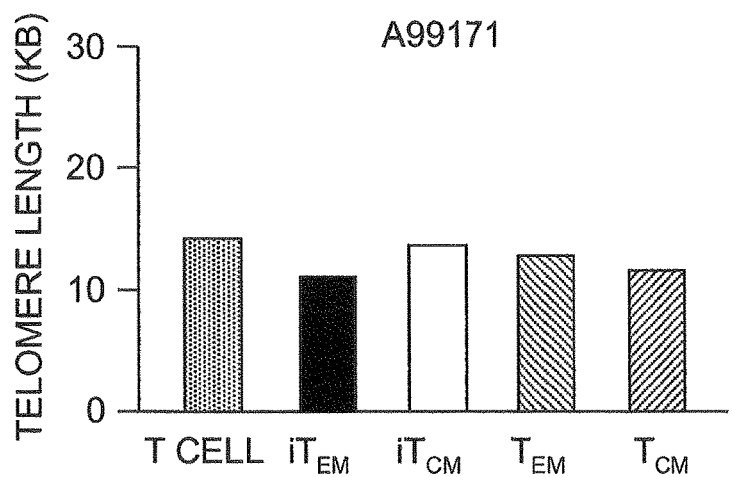

FIG. 2d. Telomere length in CMV-specific T cell clones derived from CD62L+ and CD62L− subsets. The median telomere length of duplicate samples was measured by automated flow-FISH in peripheral blood T lymphocytes (shaded squares), in the infused T cell clones (i$T_{EM}$ filled squares, i$T_{CM}$ open squares), and in each of two additional randomly selected $T_{EM}$ (left hatched squares) and $T_{CM}$-derived (right hatched squares) T cell clones from each macaque.

FIGS. 3a-3d show persistence and migration of $T_{EM}$ and $T_{CM}$-derived CD8+ $T_E$ clones in peripheral blood, bone marrow, and lymph nodes following adoptive transfer.

Figure 3A:
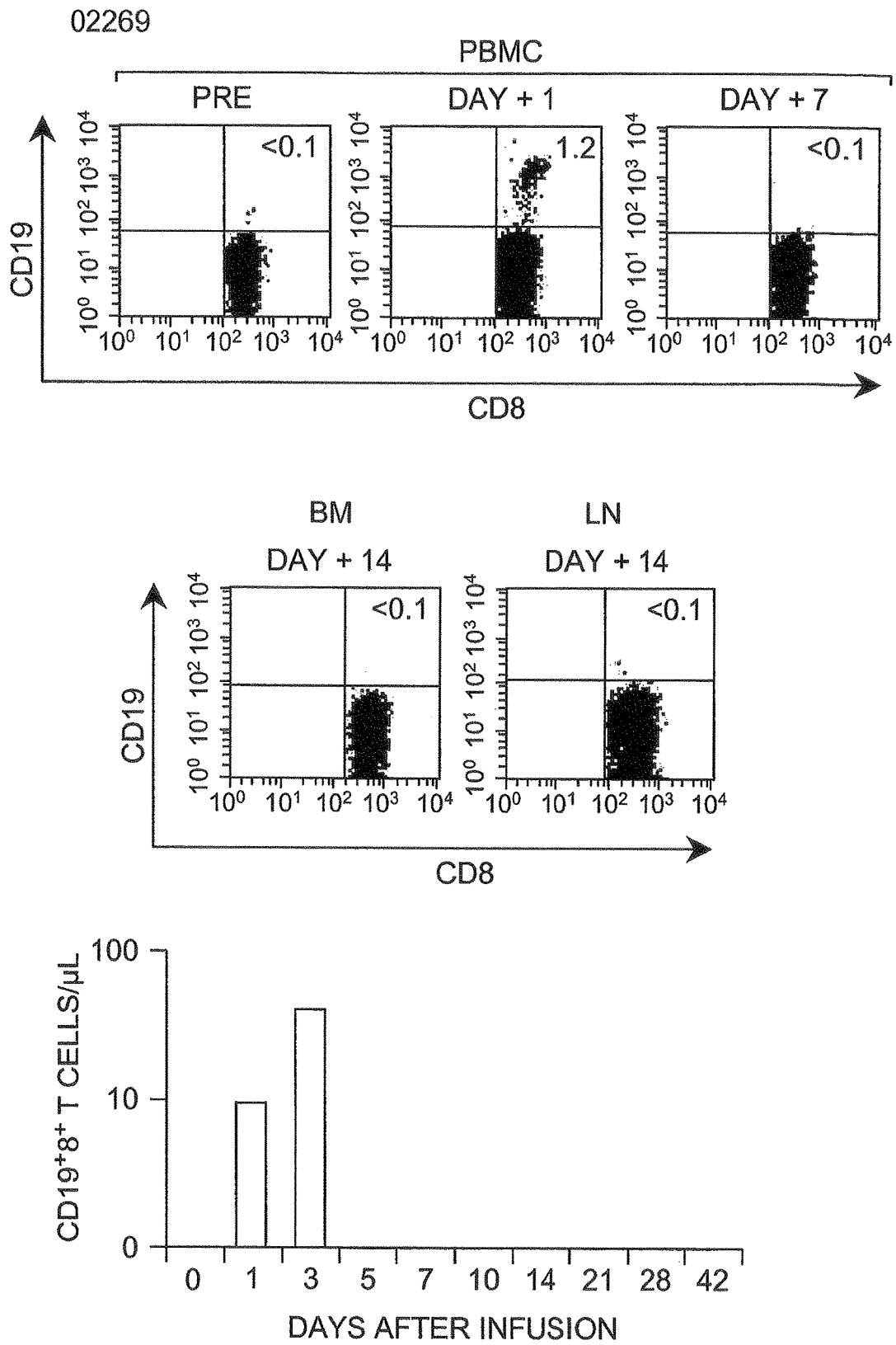
Figure 3B:
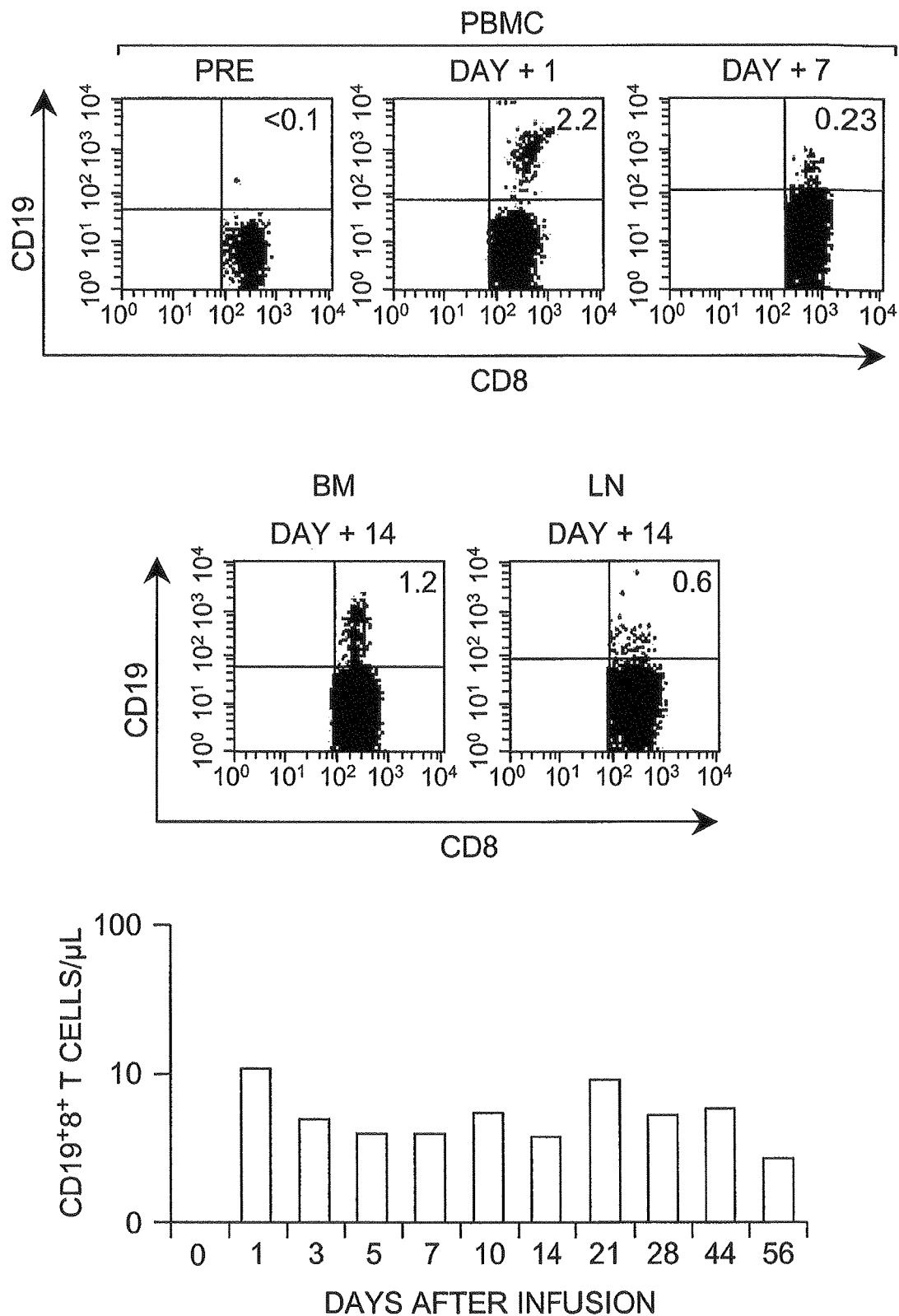

FIGS. 3a-b. In vivo persistence and migration of ΔCD19-modified $T_{EM}$-derived (a) and $T_{CM}$ derived (b) T cell clones in macaque 02269. The T cell clones were transferred in separate infusions given intravenously more than 10 weeks apart at a cell dose of 3×10$^8$/kg. Samples of PBMC were collected at intervals for 6-8 weeks after each infusion. Bone marrow and lymph node samples were collected before infusion and fourteen days after each T cell infusion. Samples were stained with fluorochrome-conjugated anti-CD3, CD8, and CD19 antibodies, respectively. The frequency of transferred CD 19+ T cells was determined by flow cytometry with gating on CD3+CD8+ cells. Left panels show the percentage of CD8+ T cells that expressed CD19 in blood, bone marrow and lymph nodes prior to and at intervals after infusion of the $T_{EM}$-derived (a) and $T_{CM}$-derived (b) T cell clones. Right panels show the absolute numbers of CD19+CD3+CD8+ T cells per μl of blood. This was determined by calculating the absolute number of CD3+CD8+ T cells per μl of blood at the indicated days (% of CD3+CD8+ T cells in an aliquot of mononuclear cells× mononuclear cell count per μl blood/100). Subsequently, the number of CD19+CD3+CD8+ T cells was derived (% CD19+ CD3+CD8+ T cells×absolute CD3+CD8+ count per μl blood/100).

Figure 3C:
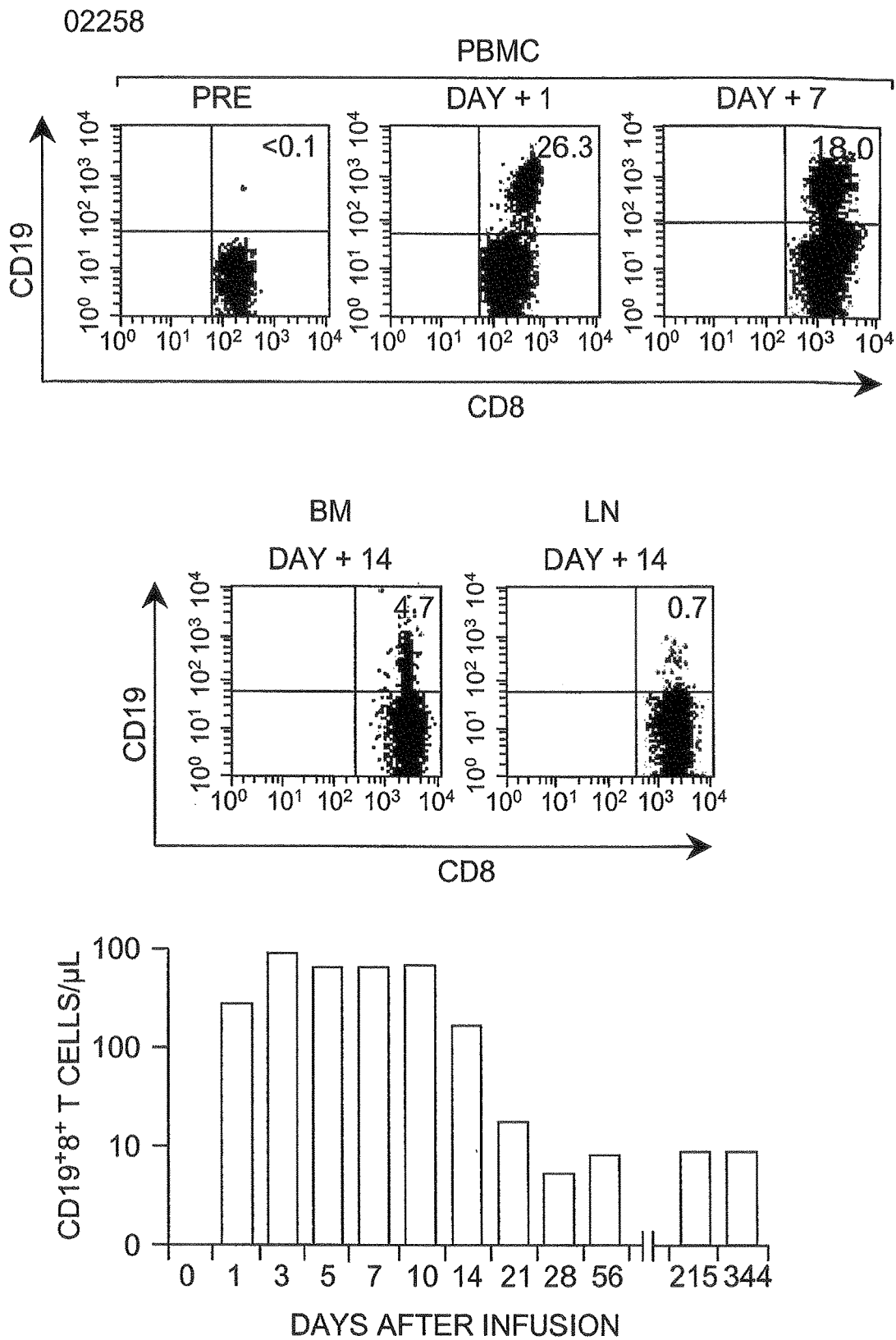
Figure 3D:
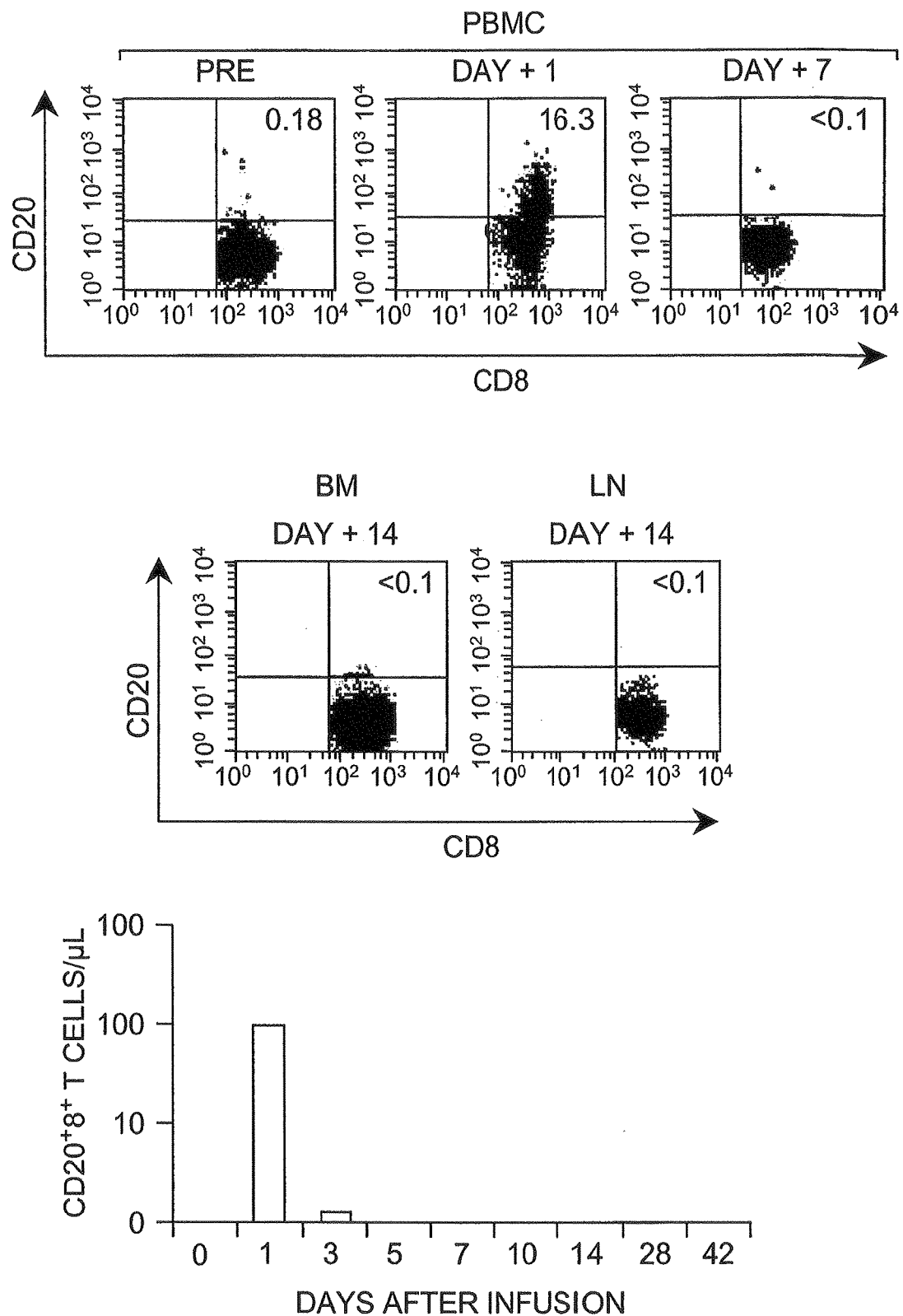

FIGS. 3c-d. In vivo persistence and migration of adoptively transferred ΔCD19-modified $T_{CM}$ derived and CD20-modified $T_{EM}$-derived T cell clones in macaque 02258. CMV-specific CD8+ T cell clones were adoptively transferred in separate intravenous infusions at a cell dose of 6×10$^8$/kg. Aliquots of blood, bone marrow, and lymph nodes were obtained before and at the indicated times after each T cell infusion and analyzed by flow cytometry using specific antibodies to detect the transferred CD19+CD8+ or CD20+ CD8+ T cells, respectively. Left panels show the percentage of CD8+ T cells that expressed ΔCD19 (c) or CD20 (d) in blood, bone marrow and lymph nodes at intervals after each infusion. Right panels show the absolute number of CD3+ CD8+ T cells per μl of blood that expressed ΔCD19 (c) or CD20 (d) at intervals after infusion.

FIGS. 4a-4e show $T_{CM}$-derived $T_E$ clones undergo less apoptosis after adoptive transfer compared with $T_{EM}$-derived $T_E$ clones, and are rescued from cell death in vitro by IL-15.

Figure 4A:
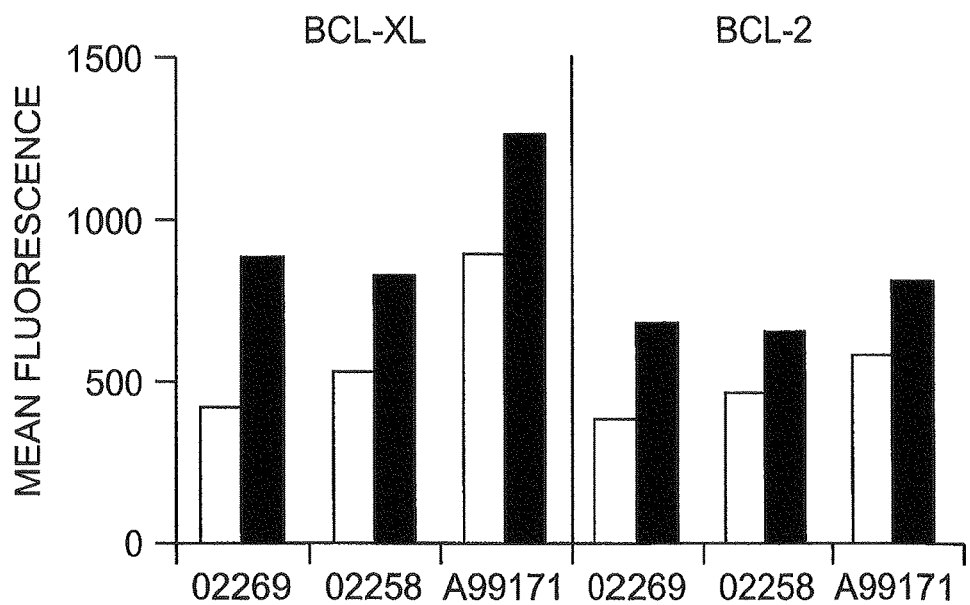

FIG. 4a. Expression of bcl-xl and bcl-2 by $T_{EM}$-derived (open squares) and $T_{CM}$-derived (filled squares) CD8+ T cell clones adoptively transferred to macaques 02269, 02258, and A99171. The T cells were analyzed at the end of a 14-day stimulation cycle by intracellular staining with bcl-xl and bcl-2 specific antibodies. The mean fluorescence intensity of staining is shown on the y axis.

Figure 4B:
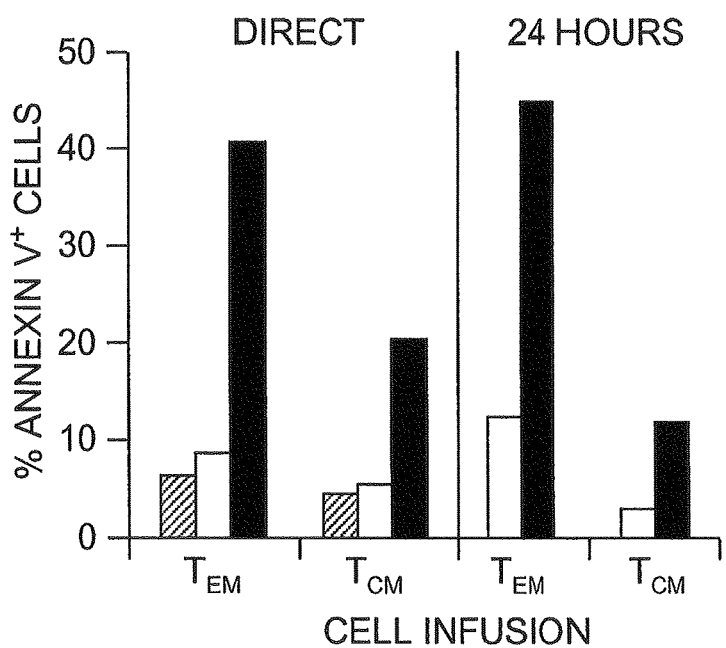

FIG. 4b. Apoptosis of $T_{EM}$-derived and $T_{CM}$-derived CD8+ $T_E$ clones in vivo. A ΔCD19-modified T cell clone derived from the CD62L $T_{EM}$ fraction was adoptively transferred at a dose of 6×10$^8$/kg to macaque A99171, followed 5 weeks later by the infusion of the same cell dose of a ΔCD19-modified T cell clone derived from the CD62L$^+$ T$_{CM}$ fraction. Samples of PBMC were obtained on day 1 after transfer and the proportion of ΔCD19-expressing CD8$^+$ T cells that bound Annexin V and/or stained positive for PI was determined by flow cytometry after staining with anti-CD8 and CD19 antibodies, and with Annexin V and PI. PBMC were analyzed directly and after 24 hours of culture in CTL media. The analysis was performed after gating on CD8$^+$CD19$^-$ T cells (open squares) and on CD8$^+$CD19$^+$ T cells (filled squares), respectively. The hatched bars show the proportion of T cells in each of the cell products prior to infusion that bound Annexin V or stained positive for PI.

Figure 4C:
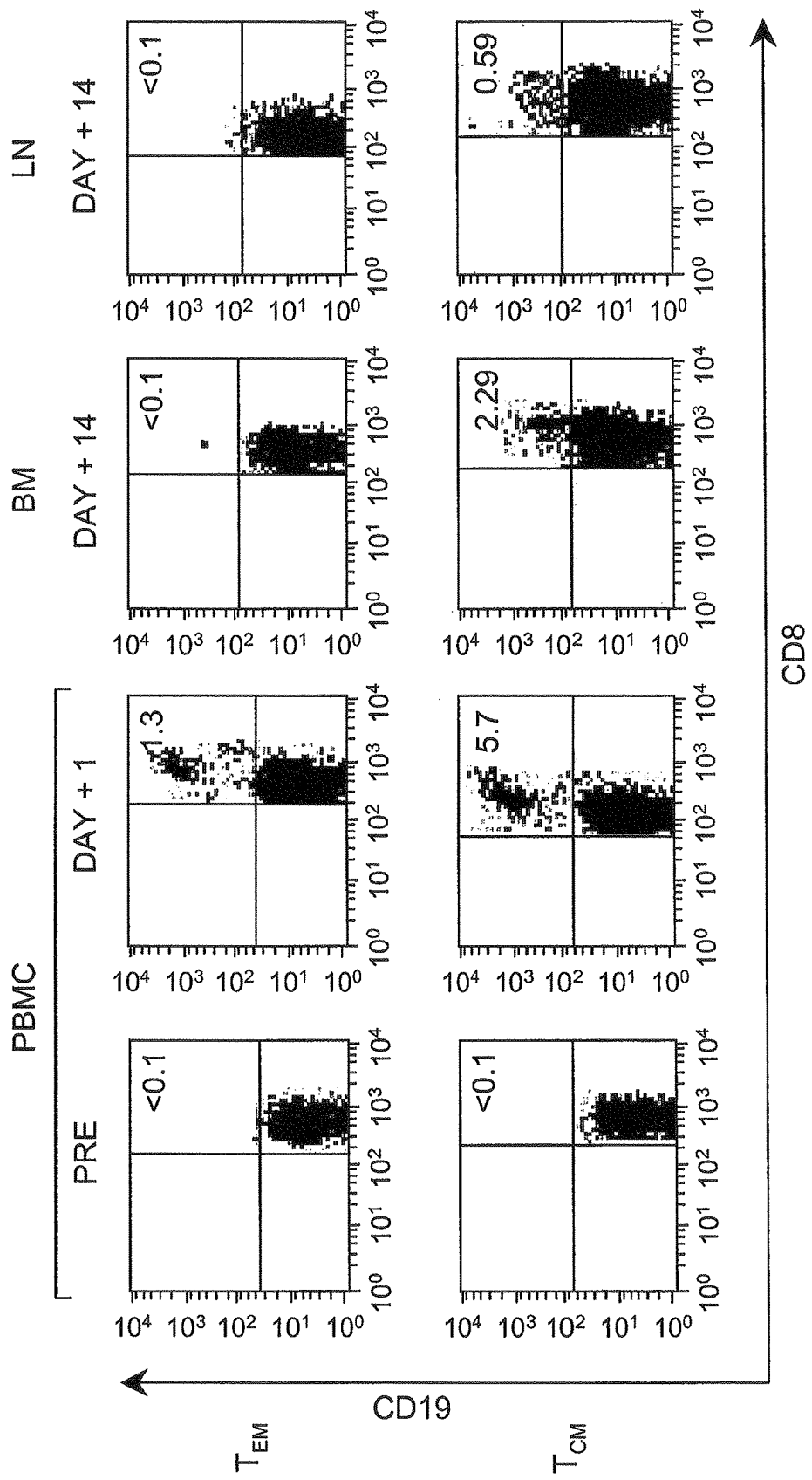

FIG. 4c. Persistence and migration of T$_{EM}$-derived and T$_{CM}$-derived T$_E$ clones in macaque A99171. Peripheral blood, bone marrow, and lymph node cells obtained at intervals after each T cell infusion were analyzed by flow cytometry to detect transferred CD19$^+$CD8$^+$ T cells. The samples were analyzed after gating on CD3$^+$CD8$^+$ cells.

Figure 4D:
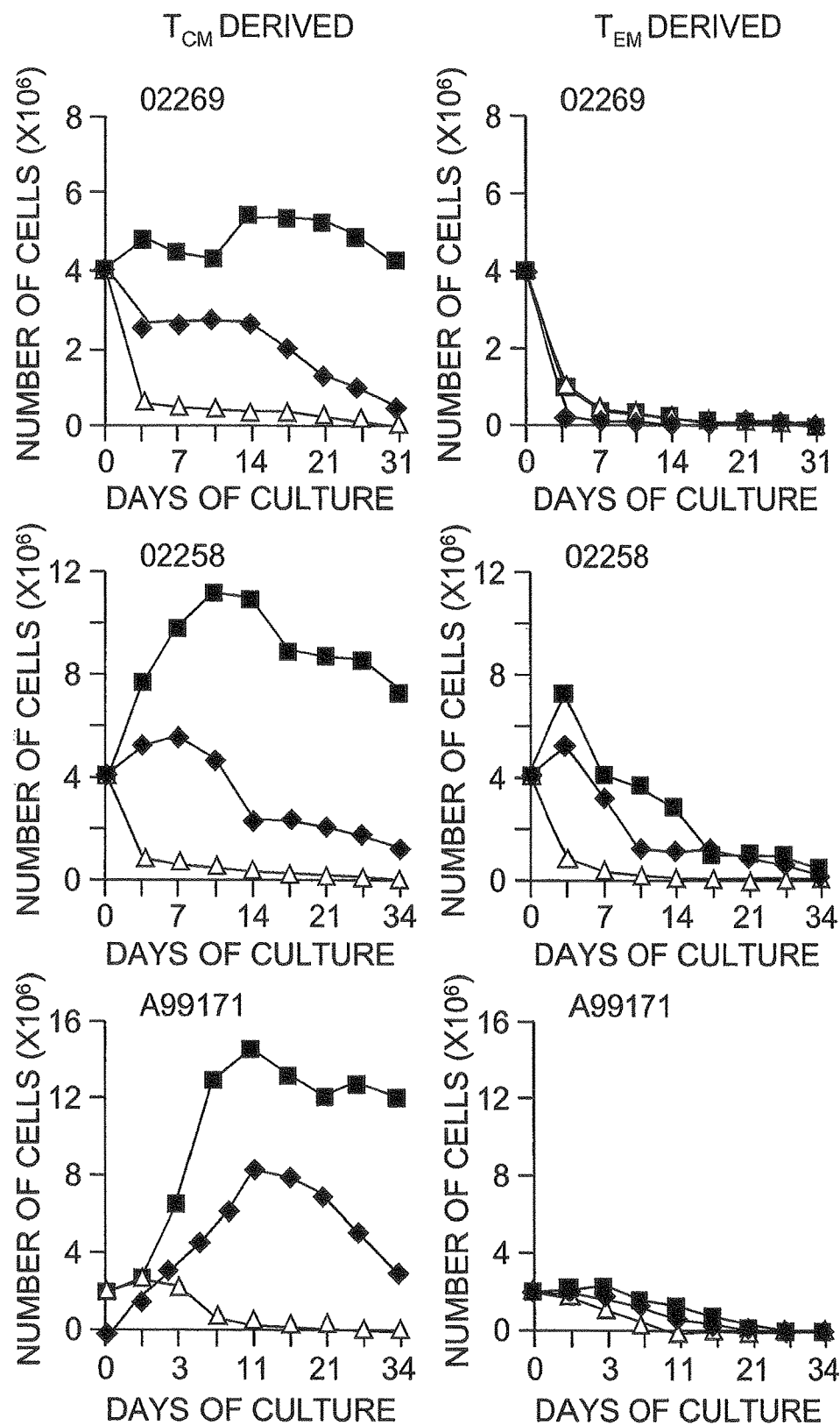

FIG. 4d. IL-15 supports the in vitro survival of T$_{CM}$-derived but not T$_{EM}$-derived CD8$^+$ T$_E$ clones. Aliquots of the CMV-specific T$_{EM}$-derived and T$_{CM}$-derived CD8$^+$ T cell clones that were used for adoptive transfer to macaques 02269, 02258, and A99171 respectively, were plated in wells containing medium alone (open triangles) or medium supplemented with IL-2 (16.6 U/ml; 1 ng/ml) (filled diamonds) or IL-15 (1 ng/ml) (filled squares), respectively. The number of viable cells was determined at the indicated days (up to 34 days) by counting cells using trypan dye exclusion.

Figure 4E:
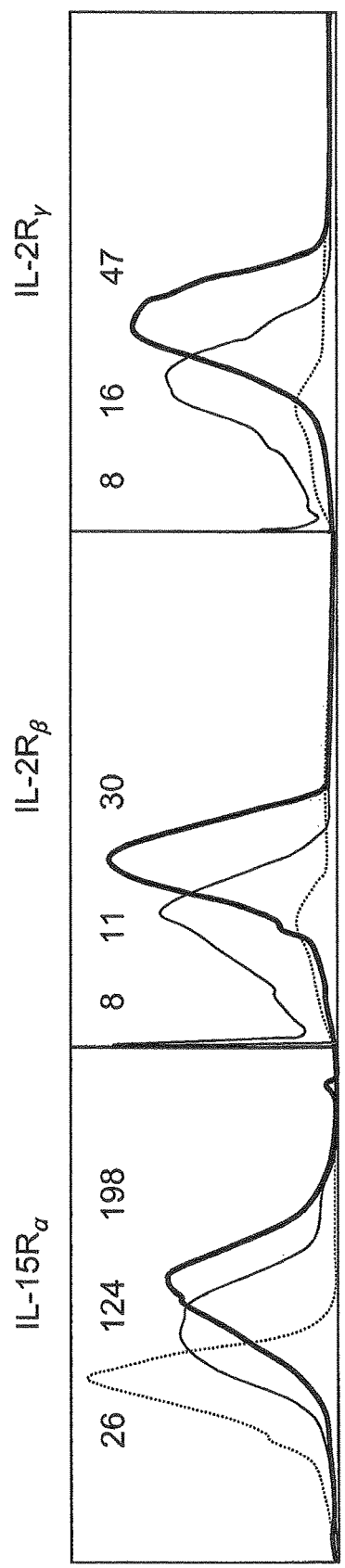

FIG. 4e. CD8$^+$ T$_{CM}$-derived clones express higher levels of IL-15 receptor (IL-15R) chains. Expression of IL-15Rα, IL-2Rβ, and IL-2Rγ on aliquots of CMV-specific T$_{CM}$-derived (bold line) and T$_{EM}$-derived (black line) T cell clones was measured by flow cytometry on day 13-14 after stimulation. Staining with isotype control antibody is shown by the dotted line. The data is shown for the T cell clones used for the adoptive transfer experiments in macaque 02269, and is representative of the data obtained for the T cell clones administered to macaques 02258 and A99171, respectively.

FIGS. 5a-5e show adoptively transferred T$_{CM}$-derived T$_E$ cells reacquire markers of T$_{CM}$ in vivo and persist in memory cell niches.

Figure 5A:
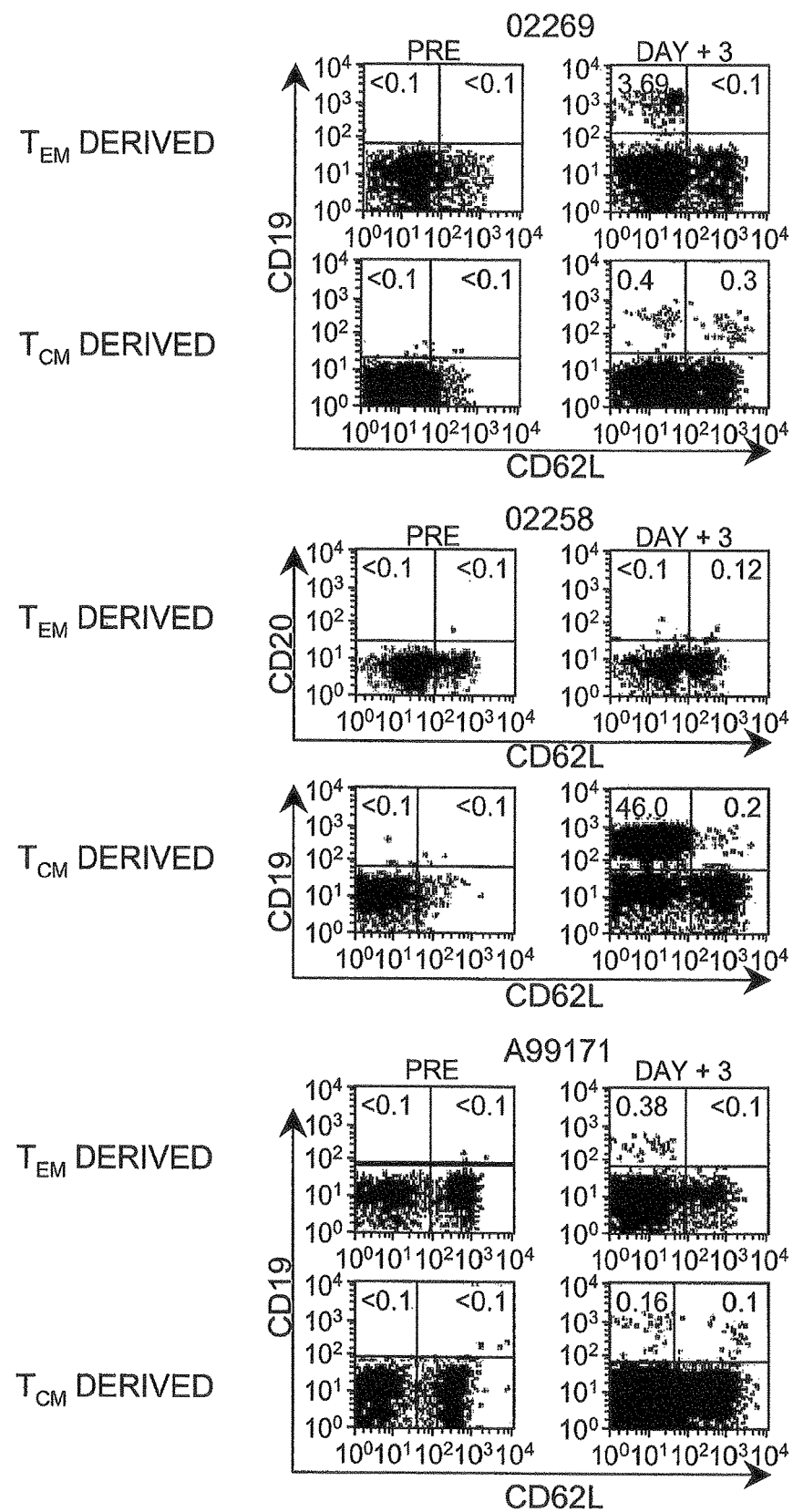

FIG. 5a. Expression of CD62L on T$_{EM}$-derived (upper panels) or T$_{CM}$-derived (lower panels) T$_E$ clones after adoptive transfer. Samples of PBMC were obtained before and on day 3 after the infusion of T$_{CM}$ and T$_{EM}$-derived T cell clones, and analyzed by flow cytometry after staining with fluorochrome-conjugated anti-CD3, CD8, CD62L, and either CD19 or CD20 antibodies. Cells were gated to identify CD3$^+$CD8$^+$ T cells and the percentage of T cells that expressed the CD19 or CD20 marker gene and CD62L is shown in the upper right quadrant of each panel.

FIGS. 5b-e. A major fraction of CD8$^+$ T cells that persist after adoptive transfer acquire phenotypic markers of T$_{CM}$ and reside in lymph nodes. Aliquots of PBMC, lymph nodes (LN), and bone marrow (BM) were obtained from macaque 02258 at day 14 and day 56 after the infusion of the ΔCD19-modified T$_{CM}$-derived CMV-specific T cell clone. The expression of phenotypic markers of T$_{CM}$ including CD62L (b), CCR7 (c), CD28 (d), and CD127 (e) on the subset of transferred CD19$^+$ T cells was determined by flow cytometry after gating on CD3$^+$CD8$^+$ cells.

FIGS. 6a-6e show adoptively transferred CD8$^+$ T cells that persist in vivo exhibit functional properties of memory T cells.

Figure 6A:
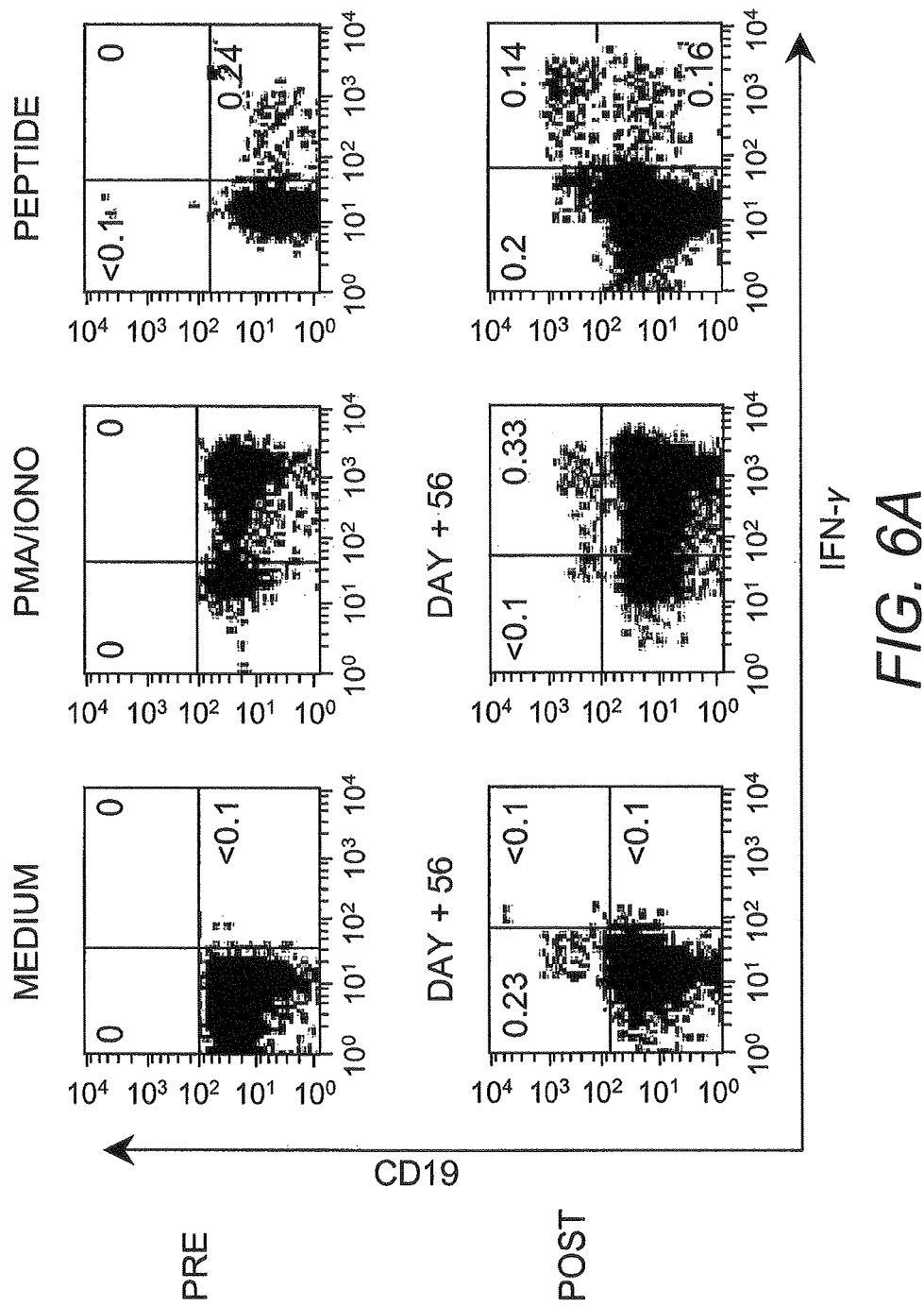

FIG. 6a. Adoptively transferred CD8$^+$ T cells that persist in vivo produce IFN-γ after antigen stimulation. PBMC were obtained before the T cell infusion (Pre) and 21 days after (Post) the infusion of a ΔCD19-modified T$_{CM}$-derived CMV-specific CD8$^+$ T cell clone. Aliquots of PBMC were stimulated with medium alone, PMA/ionomycin, or the CMV IE peptide recognized by the transferred T cell clone. IFN-γ production by CD8$^+$ T cells was examined by cytokine flow cytometry after staining with anti-CD3, CD8, CD19, and IFN-γ antibodies. The analysis was performed after gating on CD3$^+$CD8$^+$ T cells. The data is shown for macaque 02269 and is representative of a separate experiment in macaque 02258.

Figure 6B:
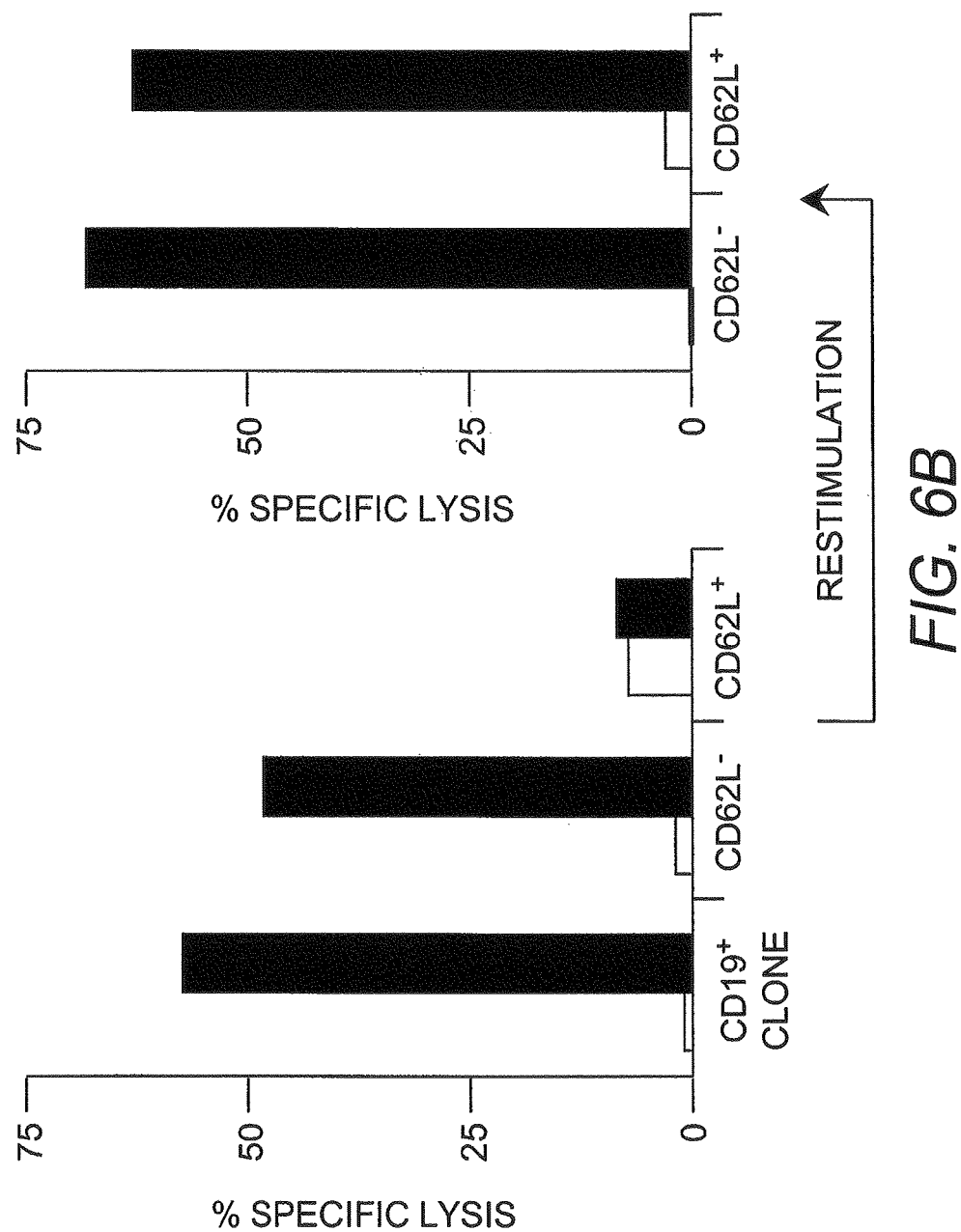

FIG. 6b. Adoptively transferred T cells that re-express CD62L lack direct cytotoxicity but differentiate into cytotoxic cells after TCR stimulation. Left panel: PBMC obtained 14-70 days after the infusion of a ΔCD19-modified T$_{CM}$-derived CD8$^+$ T cell clone were pooled and sorted into CD19$^+$CD62L$^-$CD8$^+$ and CD19$^+$CD62L$^+$CD8$^+$ fractions that were at least 80% pure. The sorted cells were examined for recognition of autologous target cells alone (open squares) or pulsed with CMV IE peptide (closed squares) in a 4-hour chromium release assay at an E/T ratio of 5:1. The lysis of target cells by the in vitro cultured T$_{CM}$-derived CD19-modified CD8$^+$ T cell clone served as a positive control. Right panel: Aliquots of the sorted CD62L$^-$ΔCD19$^+$CD8$^+$ and CD62L$^+$ΔCD19$^+$CD8$^+$ T cells were stimulated in vitro using anti-CD3 and CD28 antibodies, in the presence of γ-irradiated feeder cells and IL-2 (50 U/ml). After 14 days of culture, the cultures were assayed for recognition of peptide pulsed target cells in a 4-hour chromium release assay (E/T ratio of 5:1). The data is shown for macaque 02258 and is representative of that observed with macaque 02269.

Figure 6C:
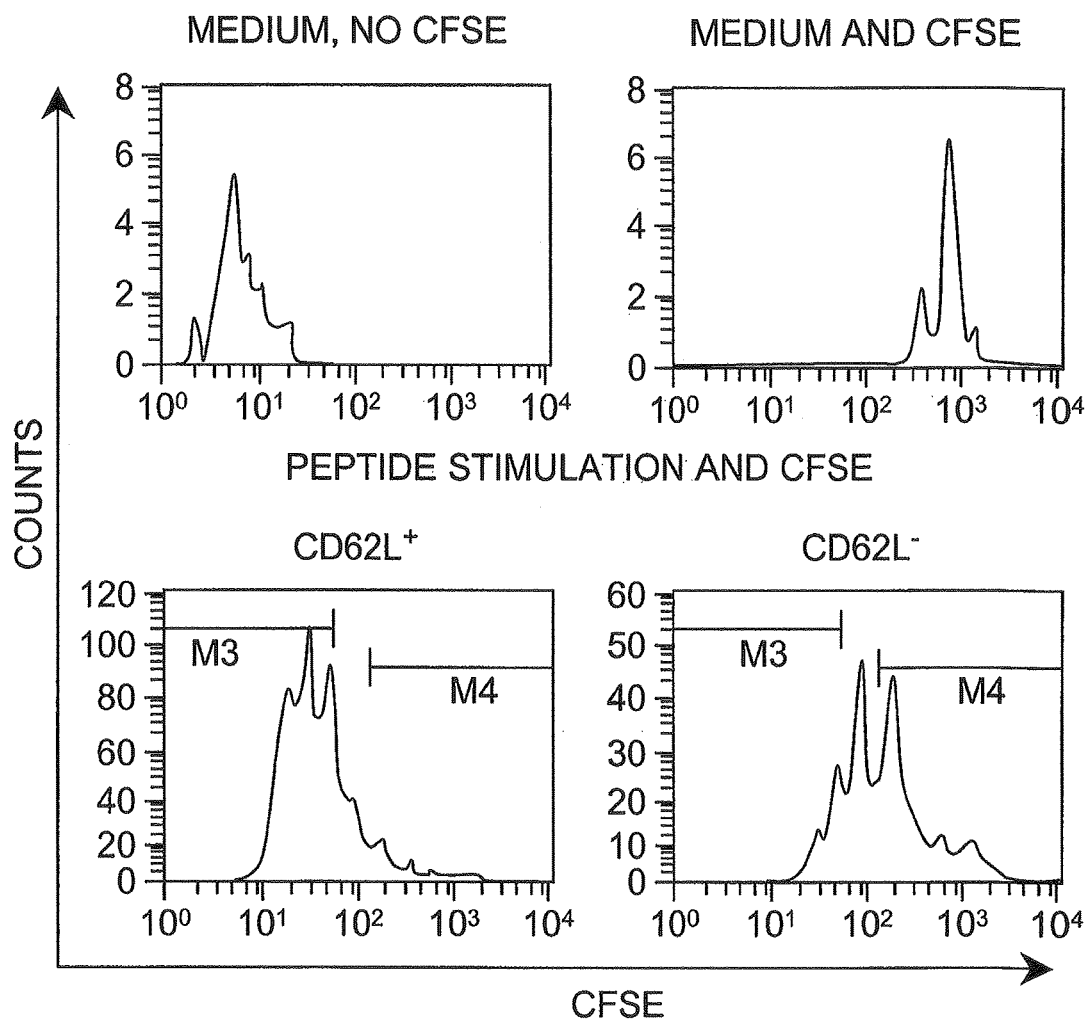

FIG. 6c. Adoptively transferred T cells that reacquire CD62L in vivo exhibit more rapid proliferation than those that remain CD62L$^-$. Aliquots of the sorted ΔCD19$^+$CD62L$^+$CD8$^+$ and ΔCD19$^+$CD62L$^-$CD8$^+$ T cells from macaque 02269 were labeled with CFSE (upper panels) and stimulated in vitro with either CMV IE peptide-pulsed autologous CD40L activated B cells or medium alone. After 5 days, dilution of CFSE was assessed by flow cytometry after gating on ΔCD19$^+$CD3$^+$CD8$^+$ cells. The M3 gate identifies cells that have undergone more than five divisions.

Figure 6D:
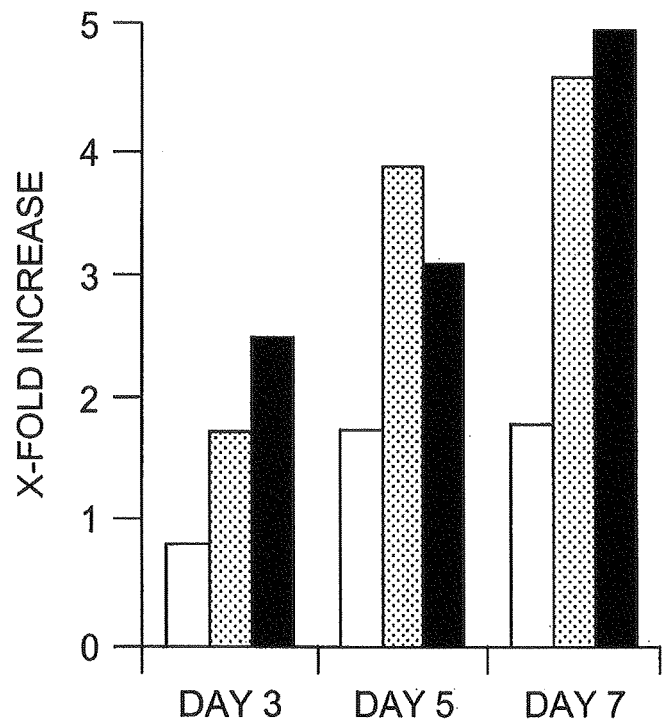

FIG. 6d. Adoptively transferred T cells can be driven to expand in vivo by the infusion of TAPC. Autologous T cells obtained and cryopreserved from macaque A99171 prior to any T cell infusions were thawed and expanded by stimulation with anti-CD3 and anti-CD28 antibodies, and IL-2. After expansion, the T cells were pulsed with the CMV IE peptide recognized by the adoptively transferred ΔCD19-modified T$_{CM}$ clone. Eight weeks after the T cell infusion when a stable level of CD19$^+$ T cells was established in vivo, a dose of 1×10$^7$ T-APC/kg was administered intravenously. The absolute number of CD3$^+$CD8$^+$ T cells and CD19$^+$CD8$^+$ T cells/μl of blood was measured on samples obtained prior to administration of T-APC, and on day +3, +5 and +7 after the infusion of T-APC. The number of endogenous IE-specific CD8$^+$ T cells was measured at the same time points by cytokine flow cytometry after gating on CD19$^-$CD3$^+$CD8$^+$ cells. The data shows the fold-increase in the absolute numbers of CD3$^+$CD8$^+$ T cells (open squares), CD19$^+$CD8$^+$ T cells (shaded squares), and CD19$^-$ IE-specific CD8$^+$ T cells (filled squares) at day +3, +5 and +7 after the infusion of T-APC.

Figure 6E:
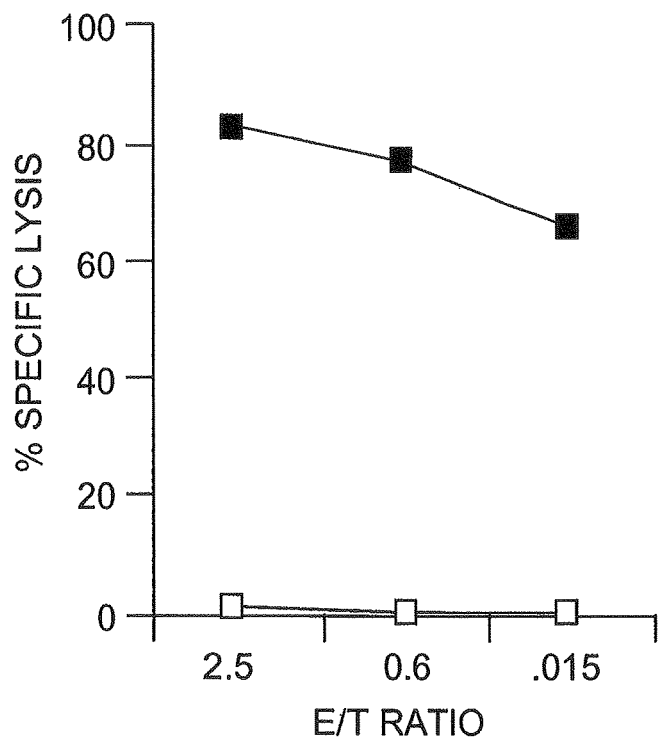

FIG. 6e. T-APC pulsed with IE peptide are lysed by IE-specific CD8$^+$ T cells. T-APC generated from macaque A99171 either pulsed with IE peptide (filled squares) or with media alone (open squares) were labeled with $^{51}$Cr and used as targets for an aliquot of the autologous IE specific CD8$^+$ T cell clone that was adoptively transferred to macaque A99171.

The present invention is explained in greater detail below. The disclosures of all United States patent references cited herein are incorporated by reference herein in their entirety.

DETAILED DESCRIPTION OF THE PREFERRED EMBODIMENTS

"T cells" or "T lymphocytes" as used herein may be from any mammalian, preferably primate, species, including monkeys, dogs, and humans. In some embodiments the T cells are allogenic (from the same species but different donor) as the recipient subject; in some embodiments the T cells are autologous (the donor and the recipient are the same); in some embodiments the T cells are syngeneic (the donor and the recipients are different but are identical twins).

Cytotoxic T lymphocyte (CTL) as used herein refers to a T lymphocyte that expresses CD8 on the surface thereof (i.e., a CD8$^+$ T cell). In some embodiments such cells are preferably "memory" T cells ($T_M$ cells) that are antigen-experienced.

"Central memory" T cell (or "$T_{CM}$") as used herein refers to a CTL that expresses CD62L on the surface thereof (i.e., CD62L+CD8$^+$ cells).

"Effector memory" T cell (or "$T_{EM}$") as used herein refers to a CTL that does not express CD62L on the surface thereof (i.e., CD62L$^-$CD8$^+$ cells).

"Enriched" and "depleted" as used herein to describe amounts of cell types in a mixture refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition may contain 60, 70, 80, 90, 85, or 99 percent or more (in number or count) of the "enriched" cells and 40, 30, 20, 10, 5 or 1 percent or less (in number or count) of the "depleted" cells.

Interleukin-15 is a known and described in, for example, U.S. Pat. No. 6,344,192.

I. In Vitro Expansion.

T lymphocytes can be collected in accordance with known techniques and enriched or depleted by known techniques such as affinity binding to antibodies such as flow cytometry and/or affinity binding. After enrichment and/or depletion steps, in vitro expansion of the desired T lymphocytes can be carried out in accordance with known techniques (including but not limited to those described in U.S. Pat. No. 6,040,177 to Riddell et al.), or variations thereof that will be apparent to those skilled in the art.

For example, the desired T cell population or subpopulation may be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). The order of additional of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least about 25 degrees Celsius, preferably at least about 30 degrees, more preferably about 37 degrees.

The T lymphocytes expanded are typically cytotoxic T lymphocytes (CTL) that are specific for an antigen present on a human tumor or a pathogen.

The non-dividing feeder cells can comprise gamma-irradiated PBMC feeder cells. In some embodiments, the PBMC are irradiated with gamma rays in the range of about 3000 to 3600 rads.

Optionally, the expansion method may further comprise the step of adding non-dividing EBV-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial T lymphocytes of at least about 10:1.

Optionally, the expansion method may further comprise the step of adding anti-CD3 monoclonal antibody to the culture medium (e.g., at a concentration of at least about 0.5 ng/ml). Optionally, the expansion method may further comprise the step of adding IL-2 and/or IL-15 to the culture medium (e.g., wherein the concentration of IL-2 is at least about 10 units/ml).

In some embodiments it may be desired to introduce functional genes into the T cells to be used in immunotherapy in accordance with the present invention. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al., describing the use of bifunctional selectable fusion genes derived from fusing a dominant positive selectable marker with a negative selectable marker. This can be carried out in accordance with known techniques (see, e.g., U.S. Pat. No. 6,040,177 to Riddell et al. at columns 14-17) or variations thereof that will be apparent to those skilled in the art based upon the present disclosure.

Various infection techniques have been developed which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), and retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral infection Retroviral vectors provide a highly efficient method for gene transfer into eukaryotic cells. Moreover, retroviral integration takes place in a controlled fashion and results in the stable integration of one or a few copies of the new genetic information per cell.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-1 TK) gene (Wigler et al., Cell 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments it may be useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine daminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374-3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See also the publications of PCT/US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

A variety of methods can be employed for transducing T lymphocytes, as is well known in the art. For example, retroviral transductions can be carried out as follows: on day 1 after stimulation using REM as described herein, provide the cells with 20-30 units/ml IL-2; on day 3, replace one half of the medium with retroviral supernatant prepared according to standard methods and then supplement the cultures with 5 ug/ml polybrene and 20-30 units/ml IL-2; on day 4, wash the cells and place them in fresh culture medium supplemented with 20-30 units/ml IL-2; on day 5, repeat the exposure to retrovirus; on day 6, place the cells in selective medium (containing, e.g., an antibiotic corresponding to an antiobiotic resistance gene provided in the retroviral vector) supplemented with 30 units/ml IL-2; on day 13, separate viable cells from dead cells using Ficoll Hypaque density gradient separation and then subclone the viable cells.

II. Compositions and Methods.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

Subjects that can be treated include subjects afflicted with cancer, including but not limited to colon, lung, liver, breast, prostate, ovarian, skin (including melanoma), bone, and brain cancer, etc. In some embodiments the tumor associated antigens are known, such as melanoma, breast cancer, squamous cell carcinoma, colon cancer, leukemia, myeloma, prostate cancer, etc. (in these embodiments memory T cells can be isolated or engineered by introducing the T cell receptor genes). In other embodiments the tumor associated proteins can be targeted with genetically modified T cells expressing an engineered immunoreceptor. Examples include but are not limited to B cell lymphoma, breast cancer, prostate cancer, and leukemia.

Subjects that can be treated also include subjects afflicted with, or at risk of developing, an infectious disease, including but not limited to viral, retroviral, bacterial, and protozoal infections, etc.

Subjects that can be treated include immunodeficient patients afflicted with a viral infection, including but not limited to Cytomegalovinis (CMV), Epstein-Barr virus (EBV), adenovirus, BK polyomavirus infections in transplant patients, etc.

Cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumen.

A treatment-effective amount of cells in the composition is at least $10^9$, typically greater than $10^9$, at least $10^{10}$ cells, and generally more than $10^{10}$. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells.

In some embodiments, the lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17.

The present invention is illustrated further in the examples set forth below.

EXPERIMENTAL

In the normal host, T cell memory persists for life indicating the capacity for selfrenewal in addition to differentiation[23]. This quality of T cell memory has been suggested to reside in the CD62L$^+$ T$_{CM}$ subset, although a unique subset of T cells that self-renew and differentiate has been identified in mice[18,23,24]. We sought to determine if T$_E$ clones differentiated in vitro from T$_{CM}$ or T$_{EM}$ subsets might differ intrinsically in their potential to persist after adoptive transfer. Here, we show in a non-human primate model relevant for human translation, that antigen-specific T$_E$ clones derived from T$_{CM}$ but not T$_{EM}$ precursors can persist, migrate to lymph nodes and bone marrow, reacquire phenotypic properties of T$_{CM}$ and T$_{EM}$, and respond to antigen challenge.

Methods

Animals and Experimental Design.

Adult macaques (*Macaca nemestrina*) were housed at the University of Washington Regional Primate Research Center, under American Association for Accreditation of Laboratory Animal Care approved conditions. The Institutional Animal Care and Use Committee approved the experimental protocols.

Healthy macaques were selected for this study if they had evidence of prior CMV infection as determined by a positive lymphoproliferative response to CMV antigen and a CD8$^+$ T cell response to CMV IE-1 or IE-2 peptides[25]. CMV-specific CD8$^+$ T cell clones were isolated from CD62L$^+$ CD8$^+$ and CD62L$^-$CD8$^+$ T cells obtained by cell sorting of PBMC from each macaque, modified by retroviral gene transfer, expanded in vitro and infused intravenously at cell doses of 3-6×10$^8$/kg. Blood samples were obtained by venipuncture at intervals after each infusion and bone marrow from the posterior iliac crest and a lymph node from the inguinal region were obtained under anaesthesia.

Accredited clinical laboratories performed CBC and serum chemistry on blood obtained before and at intervals after each T cell infusion. The macaques were followed for at least 7 weeks after each T cell infusion.

Cytokine Flow Cytometry for Detection of CMV-Specific CD8$^+$ T Cells.

PBMC were isolated from peripheral blood by Ficoll-Hypaque gradient separation. Multiparameter flow cytometry was used to detect CD8$^+$ T cells in PBMC that expressed intracellular IFN-γ after stimulation with pools of 15-mer synthetic peptides with an 11 amino acid (aa) overlap that spanned the 558 aa sequence of the rhCMV IE1 protein (GenBank accession number: M93360), or with an IE-2 peptide kindly provided by Dr. L. Picker (Oregon Health Sciences University)[25]. The peptides that comprised the panel were synthesized using standard FMOC chemistry (NMI) and arranged in an analytic grid composed of 24 pools, each containing 11-12 peptides. Aliquots of PBMC were stimulated for 6 hours at 37° C. with the peptide pools (5 µg/ml) or medium alone in the presence of 1 µg/ml monoclonal anti-CD28 and anti-CD49d antibodies. Stimulation with PMA (10 ng/ml; Sigma) and ionomycin (1 µg/ml; Sigma) was performed as a positive control. After two hours, Brefeldin A (10 µg/ml; Sigma) was added. The cells were first stained with phycoerythrin (PE)-labeled anti-CD8β (Immunotech Coulter) and peridinin chlorophyll protein (Percp)-Cy5.5-labeled anti-CD4, then permeabilized using Cytofix/Cytoperm Permeabilization Solution (BD Biosciences (BD)), and stained with a fluorescein isothiocyanate (FITC)-labeled anti-IFN-γ antibody (BD). All analyses were performed on a FACSCalibur and the data analyzed using CellQuest Software (BD). Immunogenic CMV peptides were identified by the responses of CD8$^+$ T cells to intersecting peptides in the grid and the assays were repeated with each individual peptide and derivative 9-mer peptides to confirm and map specificity.

To determine if CD8$^+$ T cells for CMV IE peptides were present in the T$_{CM}$ and T$_{EM}$ subsets, PBMC were stained with fluorochrome conjugated anti-CD8 and anti-CD62L monoclonal antibodies, and CD62L$^+$CD8$^+$ T cells and CD62L$^-$CD8$^+$ T cells were sorted using a Vantage BD cell sorter. The sorted cells were assayed by cytokine flow cytometry after stimulation with autologous B cells that were activated by culture on NIH 3T3 cells modified to express human CD40L, and then pulsed with individual IE peptides or with media alone. The CD40L-activated B cells were cocultured with the purified CD62L$^+$CD8$^+$ and CD62L$^-$CD8$^+$ T cells for 6 hours prior to the addition of Brefeldin A for an additional 4 hours, followed by permeabilization and staining for intracellular IFN-γ.

Retroviral Vectors.

A truncated macaque CD 19 gene encoding for the extracellular and transmembrane domain (ΔCD19) and four aa of the cytoplasmic tail to abrogate signaling, and the full length CD20 gene were amplified by RT-PCR from cDNA generated from macaque PBMC and cloned into pcDNA3.1 vector (Invitrogen). The ΔCD19 and CD20 genes were subcloned into the retroviral plasmid pMP71 GFP$_{pre}$ (W. Uckert, Max-Delbruck-Center, Berlin, Germany) after removing the GFP gene[43]. Retrovirus supernatant was produced in the packaging cell line Phoenix Galv (G. Nolan, Stanford University, USA) after transfection using Fugene G according to the manufacturer's instruction (Roche Diagnostics).

Culture and Genetic Modification of CMV-Specific CD8+ T Cell Clones for Adoptive Transfer.

CD62L+CD8+ and CD62L-CD8+ T cell fractions were resuspended in RPMI 1640 supplemented with 25 mM HEPES, 10% human AB serum, 25 µM 2-mercaptoethanol, and 4 mM L-glutamine (T-cell media), and co-cultured with autologous monocytes pulsed with CMV IE-1 or IE-2 peptides (1 µg/ml). IL-2 (10 U/ml; Chiron Corporation) was added on day 3 of the culture. On day 7, T cell clones were generated by plating 0.3 T cells per well in 96-well round bottom plates with $1 \times 10^5$ γ-irradiated autologous PBMC pulsed with CMV IE-1 or IE-2 peptides (0.5 µg/ml) and $1 \times 10^4$ γ-irradiated B-lymphoblastoid cells (LCL) as feeder cells in the presence of 50 U/ml IL-2.

After 14 days, an aliquot from cloning wells with visible growth was tested in a chromium release assay for recognition of autologous target cells either pulsed with CMV peptide or with medium alone. T cell clones that only lysed peptide pulsed target cells were expanded by stimulation with monoclonal anti-CD3 and anti-CD28 antibodies in the presence of human γ-irradiated PBMC and EBV transformed LCL, and IL-2 (50 U/ml) as described[44,45]. On day 2 after stimulation, the cells were pelleted, resuspended in ΔCD19 or CD20 retroviral supernatant with IL-2 (50 U/ml) and polybrene (5 µg/ml), centrifuged at 1000 g for 1 hour at 32° C., and incubated overnight. The cells were then washed and cultured in CTL medium containing IL-2. On day 6 after retroviral transduction, T cells that expressed the ΔCD19 or CD20 transgene were selected with immunomagnetic beads. Briefly, the transduced T cells were incubated with monoclonal anti-CD 19 (Immunotech Coulter) or anti-CD20 antibody (BD), washed, incubated with rat anti-mouse IgG-coupled magnetic beads (Miltenyi Biotec), and selected using the MidiMACS device. The selected cells were then cultured for an additional 6 days and cryopreserved in aliquots that could be thawed subsequently for adoptive transfer experiments. The clonality of the infused T cell clones was confirmed by analysis of TCR Vβ gene rearrangements.

To assess cell viability in vitro, aliquots of the T cell clones at the end of the 14-day stimulation cycle and immediately prior to adoptive transfer were plated in 12-well tissue culture plates at 2-4. $10^6$ cells/well in T-cell media alone, media with IL-2 (1 ng/ml or 16 U/ml; Chiron), IL-15 (1 ng/ml; R&D Systems), or IL-7 (10 ng/ml; R&D).

The viability of T cells was assessed every 3-4 days by trypan blue dye exclusion. In some experiments, aliquots of the T cell clones were cultured with media containing IL19 21 (30 ng/ml) (R&D) or cocultured with autologous PBMC and mature monocytederived dendritic cells[46].

Generation of T-APC.

To generate T-APC, we expanded aliquots of autologous polyclonal T cells by stimulation with anti-CD3 and anti-CD28 monoclonal antibodies and IL-2 (50 U/ml). At the end of a 14 day stimulation cycle, the T cells were harvested, pulsed for 30 min with 1 µg/ml of the cognate CMV IE peptide, washed twice in media, suspended in normal saline and administered to the animal by intravenous infusion at a cell dose of $1 \times 10^7$/kg. An aliquot of the autologous T cells before and after pulsing with the CMV IE peptide were labeled with $^{51}$Cr and tested as targets for the CMV-specific T cell clone.

Cytotoxicity Assays.

Cytotoxic responses of CMV-specific T cells were examined as described[44,45,47]. Briefly, autologous $^{51}$Cr-labeled T cells were pulsed overnight with peptide antigen at various concentrations or medium alone and used in a chromium release assay for recognition by CD$^{8+}$ T cell clones.

Flow Cytometry.

PBMC and T cell clones were analyzed by flow cytometry after staining with fluorochrome-conjugated monoclonal anti-CD3 (SP34), CD4, CD8, CD27, CD28, CD45RA, CD62L, CCR7, CD122 (IL2-R(3), CD132 (IL2-Rγ) (BD), CD19, CD8β, CD45RO, and CD127 (Immunotech Coulter), and IL15R<(R&D) antibodies. For intracellular staining, cells were suspended in CYTOFIX/CYTOPERM™ Permeabilization Solution (BD) according to the manufacturer's instruction and stained with monoclonal antibodies to granzyme B (BD), perforin (Kamiya Biomedical), bcl-2 (BD), and bcl-xl (Southern Biotech). Isotype-matched irrelevant control monoclonal antibodies served as controls (BD). In some experiments, samples of PBMC were labeled with anti-CD8-FITC and anti-CD 19 allophycocyanin (APC) and stained with Annexin V-PE and PI according to the manufacturer's instruction. All analyses were performed on a FACSCalibur and the data analyzed using CellQuest Software (BD).

CFSE-Labeling of T Cells.

CD19+CD62L+CD8+ and CD19+CD62L-CD8+ T cells were flow sorted from pooled PBMC samples obtained after adoptive transfer and labeled with 0.625 µM CFSE (Molecular Probes) in PBS for 10 minutes at 37° C. under constant agitation, followed by blocking with 20% FCS medium. CFSE-labeled T cells were plated at $1 \times 10^5$ cells/well in a 96-well plate with autologous CD40L activated B cells ($2.5 \times 10^4$ cells/well) pulsed with 200 ng/ml CMV IE peptide. CFSE dilution was analyzed by flow cytometry after five days.

Fluorescent Probe PCR.

PCR amplifications and analyses were performed using a quantitative real-time PCR assay (Perkin-Elmer Applied Biosystems)[45,48]. DNA (0.3-1 µg) was amplified in duplicate using PCR primers and TaqMan probes (Synthegen) designed to detect a unique MP71CD20$_{pre}$ sequence using a fluorescent-tagged probe encompassing the junction of the CD20 gene and the retroviral vector pMP71$_{pre}$.

Standards consisted of DNA derived from the infused CD20+ T cells. Aliquots of preinfusion PBMC served as negative control.

Telomere Length Analysis.

The average length of telomere repeats in individual lymphocytes was measured by automated flow-FISH as described[59, 50]. Cells, which were previously frozen in 10% (v/v) DMSO 20% (v/v) human serum, were thawed and processed in microtiter plates for automated flow-FISH. Cells were hybridized with or without 0.3 µg/ml telomere specific FITC-conjugated (CCCTAA)$_3$ PNA probe, washed and counterstained with 0.01 µg/ml LDS 751 (Exciton Chemical). To convert the fluorescence measured in sample cells hybridized with the FITC-labeled telomere PNA probe into kilobases (kb) of telomere repeats, fixed bovine thymocytes with known telomere length as an internal control were processed simultaneously with each sample[50]. FITC-labeled fluorescent beads were used to correct for daily shifts in the linearity of the flow cytometer and fluctuations in the laser intensity and alignment. Flow cytometric data collection was performed on a FACSCalibur™ apparatus and the data analysis was performed using a CellQuestPro™ data analysis system (BD).

Results

Characterization of Cytomegalovirus (CMV)-Specific CD8+ T Cell Clones Derived from CD62L+ $T_{CM}$ and CD62L− $T_{EM}$ Subsets.

Immunocompetent *Macaca nemestrina* with latent CMV infection were used in this study. To identify CMV-specific CD8+ T cells, we stimulated aliquots of peripheral blood mononuclear cells (PBMC) from four macaques with rhesus CMV immediate early (IE)-1 or IE-2 peptides and analyzed interferon-gamma (IFN-γ) production by flow cytometry[25]. After identification of an immunogenic CMV epitope for each macaque, we evaluated whether specific CD8+ T cells were present in CD62L+ and CD62L− T cell fractions, purified from PBMC and containing $T_{CM}$ and $T_{EM}$ respectively. Stimulation of CD62L+ and CD62L− T cells with CMV peptides identified CD8+ T cells that produced IFN-γ in both subsets (FIG. 1a). The majority of CD62L+ T cells were positive for CCR7 and CD28, and expressed absent or low levels of granzyme B. The CD62L− T cells were mostly negative for CD28 and CCR7, and positive for granzyme B (not shown).

We next generated CD8+ CMV-specific T cell clones for adoptive transfer from purified CD62L+CD8+ ($T_{CM}$) and CD62L− CD8+ ($T_{EM}$) cells of three macaques (FIG. 1b). Cytolytic CD8+ CMV-specific T cell clones were obtained from both $T_M$ subsets in all macaques. The cloning efficiency was 13.6-23.2% for cultures initiated from $T_{CM}$, and 0.4-10.4% for cultures initiated from $T_{EM}$. Individual T cell clones were transduced with a retroviral vector encoding either a truncated cell surface CD19 (ΔCD19) or full-length CD20 molecule to permit tracking the cells in vivo, and transduced T cells were selected with immunomagnetic beads (FIGS. 1c, d). A pair of $T_{CM}$ and $T_{EM}$-derived clones was randomly selected from each of the three macaques, and expanded in culture to >5×10⁹ cells over a total culture duration of 49 days before adoptive transfer. Independent of their derivation from CD62L+ or CD62L− cells, all of the CMV-specific T cell clones had differentiated to $T_E$ and were negative for CD62L, CCR7, CD28, and CD127, and positive for granzyme B and perforin (FIG. 2a). The T cell clones of each pair recognized the same CMV peptide, had comparable avidity, displayed nearly identical growth after T cell receptor (TCR) stimulation, and had similar telomere lengths (FIGS. 2b-d).

In Vivo Persistence of CD8+ $T_E$ Clones Derived from CD62L+ $T_{CM}$ or CD62L− $T_{EM}$.

We administered the autologous gene-modified T cells intravenously and measured their frequency in the blood, lymph node, and bone marrow at intervals after infusion. A ΔCD19-modified T cell clone derived from $T_{EM}$ was transferred to macaque 02269 at a dose of 3×10+ T cells/kg, which is approximately 5-10% of the macaque total body lymphocyte pool[26]. CD19+CD8 T cells were easily detected in the blood one day after the infusion at a frequency of 1.2% of CD8+ T cells or 10 cells/μl of blood. The CD19+ T cells in the blood peaked at 3.7% of CD8+ T cells (40 cells/μl) on day three after the infusion. However, the T cells were not detected in blood obtained at day five or multiple times up to forty-two days after infusion, and were not present in bone marrow or lymph node samples obtained fourteen days after the infusion (FIG. 3a). We transferred the same dose of a ΔCD19-modified CMV-specific T cell clone derived from the $T_{CM}$ subset to this macaque. On day one post infusion, the frequency of CD 19+CD8+ T cells in the blood was 2.2% of CD8+ T cells (10 cells/μl). In contrast to the $T_{EM}$-derived clone, the $T_{CM}$-derived cells persisted in the blood for greater than fifty-six days after infusion at ~0.2% of CD8+ T cells (3-6 cells/μl), and comprised 1.2% and 0.6% of CD8+ T cells in bone marrow and lymph node samples respectively, obtained fourteen days after the infusion (FIG. 3b). In a second macaque, we infused a ΔCD19-modified $T_{CM}$-derived clone first at a higher cell dose of 6×10⁸/kg. With this dose, transferred cells were detected in the blood at a frequency of 26.3% of CD8+ T cells (228 cells/μl) on day one and 46.3% of CD8+ T cells (734 cells/μl) on day three. The transferred $T_{CM}$-derived clone was present in the bone marrow and lymph node obtained on day fourteen at 4.7% and 0.7% of CD8+ T cells, respectively (FIG. 3c). The frequency of the transferred cells in the blood declined gradually over twenty-eight days to a stable level of 7-10 cells/μl that persisted for greater than eleven months after infusion (FIG. 3c). We administered the same dose of a $T_{EM}$-derived clone transduced to express CD20 to enable the cells to be tracked and distinguished from the previously transferred ΔCD19-modified T cells. The frequency of CD20+CD8+ T cells in the blood one day after the infusion was 16.3% of CD8' T cells (103 cells/μl), but the transferred cells disappeared from the blood by day five and were not detected in the bone marrow and lymph node obtained fourteen days after the infusion (FIG. 3d). The disappearance of CD20-modified T cells was confirmed by PCR for vector sequences on DNA isolated from peripheral blood, bone marrow and lymph node mononuclear cells obtained on day 14 (data not shown).

CD8 $T_E$ Cells Derived from $T_{EM}$ Undergo Rapid Apoptosis after Adoptive Transfer and Respond Poorly to IL-15.

The failure of $T_E$ clones derived from $T_{EM}$ to persist in blood, marrow or lymph nodes after adoptive transfer could be due to cell death in vivo and/or migration to other tissue sites. $T_{EM}$-derived clones expressed lower levels of the anti-apoptotic proteins bclxl and bcl-2 than $T_{CM}$-derived clones, suggesting they may be more susceptible to apoptosis (FIG. 4a). Therefore, we infused a ΔCD19-modified $T_{EM}$-derived T cell clone to the third macaque and measured the proportion of transferred cells in PBMC that were positive for propidium iodide (PI) and Annexin V binding[27]. Approximately 40% of the CD19+CD8+ T cells in PBMC were PI and/or Annexin V positive when analyzed directly on day one, and 45% were positive after culturing the PBMC for 24 hours (FIG. 4b).

Consistent with the prior animals, the $T_{EM}$-derived clone was only detected in the blood for three days, and was not present in the day fourteen bone marrow or lymph node samples (FIG. 4c). We then infused a ΔCD19-modified $T_{CM}$-derived T cell clone into the same animal and analyzed the proportion of apoptotic cells. Less than 20% of the transferred Tem cells were PI and/or Annexin V positive in PBMC analyzed directly, and this fraction decreased to 12% after 24 hours of culture (FIG. 4b). The $T_{CM}$-derived clone migrated to the bone marrow and lymph nodes (FIG. 4c), and persisted in the blood for greater than seventy-seven days as observed previously (data not shown). We reasoned that the selective survival of $T_{CM}$-derived T cells in vivo might be due to responsiveness to homeostatic cytokines such as IL-15 that maintain endogenous CD8+ memory T cells[28-30], and cultured aliquots of the $T_{CM}$ and $T_{EM}$-derived clones in media containing low doses of IL-15, IL-2, or IL-7. Both $T_{EM}$ and $T_{CM}$-derived $T_E$E clones lacked expression of IL-7Rα (FIG. 2a) and died rapidly in vitro when cultured in IL-7 or in media alone (FIG. 4d). Culture in IL-15 or IL-2 also did not improve the viability of $T_{EM}$-derived clones (FIG. 4d). By contrast, $T_{CM}$-derived clones were rescued from cell death for over 30 days in IL-15 and exhibited improved survival in IL-2 (FIG. 4d). The responsiveness of $T_{CM}$-derived clones to IL-15 correlated with higher levels of cell surface IL-15Rα, IL-2Rβ®, and IL-2Rγ compared with $T_{EM}$-derived clones (FIG. 4e).

Adoptively Transferred CD8$^+$ $T_E$ Clones Derived from $T_{CM}$ Acquire a Memory Phenotype In Vivo.

Figure 5B:
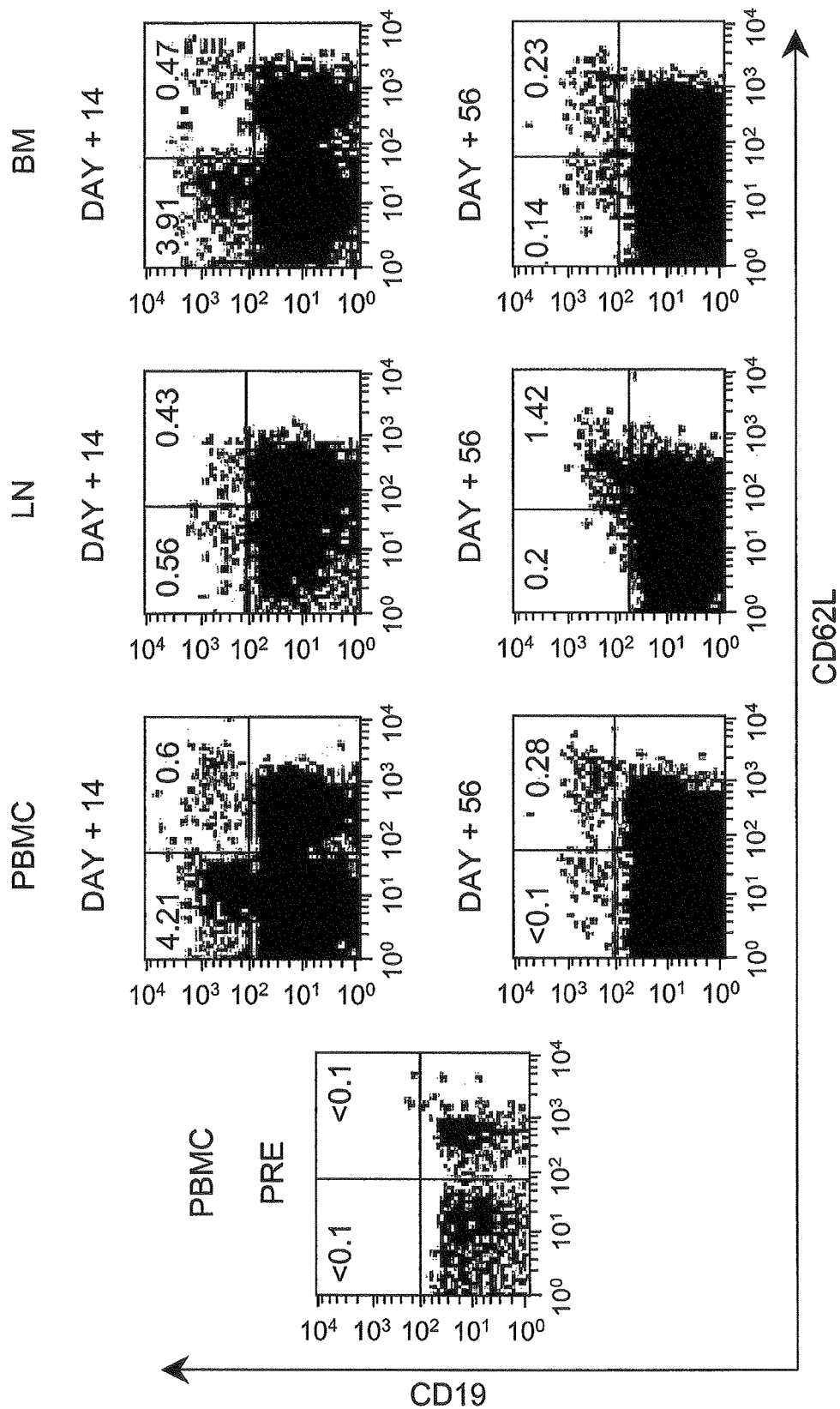

The migration of $T_{CM}$-derived CD8$^+$ $T_E$ clones to lymph nodes suggested that CD62L might be re-expressed on transferred cells in vivo. CD62L was not detected on the T cell clones at the time of adoptive transfer (FIG. 2a), or after culture in the absence of antigen stimulation with cytokines (IL-2, IL-7, IL-15, IL-21), autologous PBMC, or monocyte-derived dendritic cells (data not shown). However, in all three macaques, CD19$^+$CD62L$^+$CD8$^+$ cells were observed in the blood as early as three days after the infusion of the $T_{CM}$-derived clones and were detected in the blood, bone marrow and lymph node samples obtained on day 14 (FIG. 5a, b). The proportion of transferred T cells that were CD62L$^+$ in the lymph node was greater than in blood or marrow (FIG. 5b).

Figure 5C:
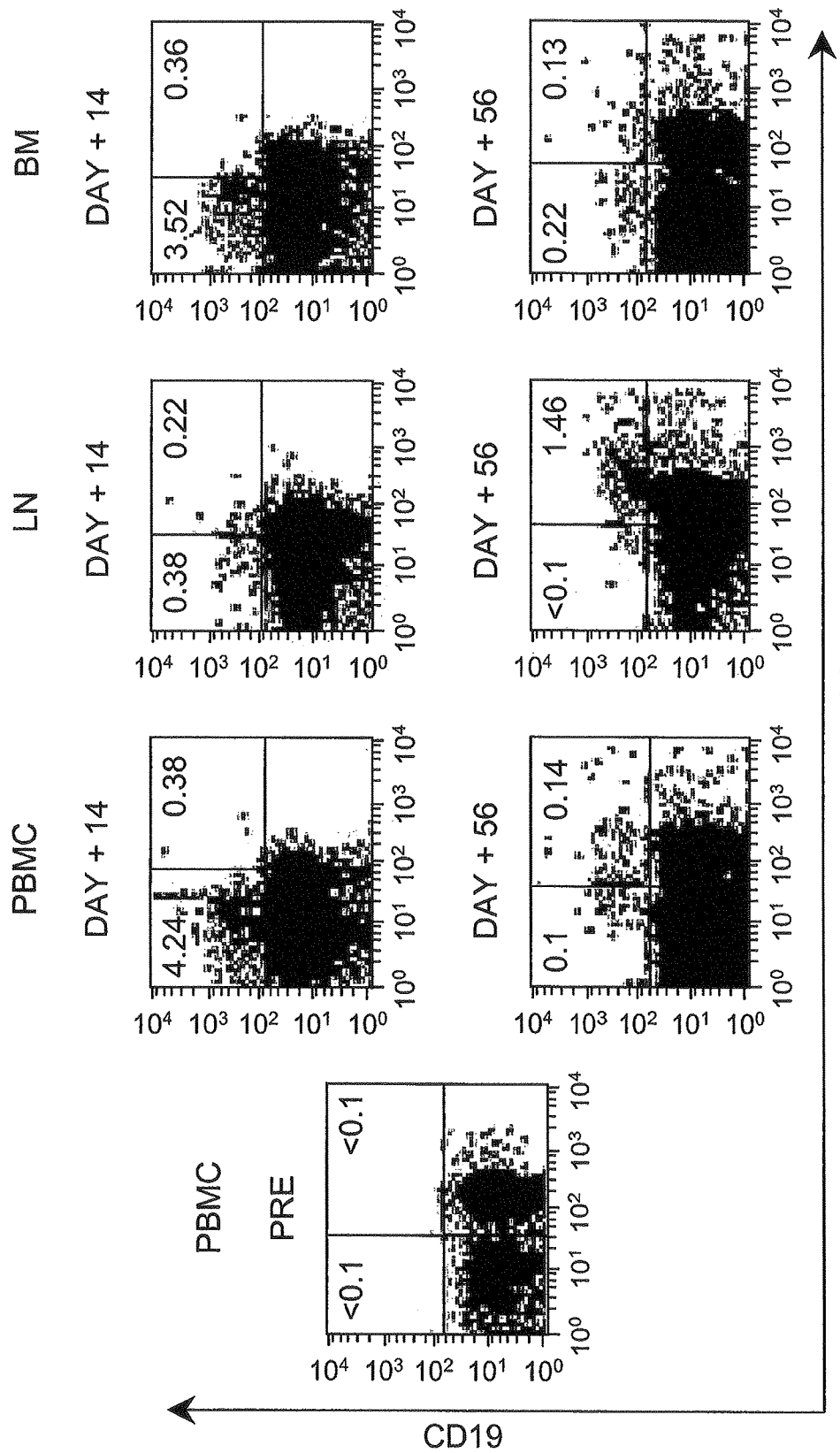
Figure 5D:
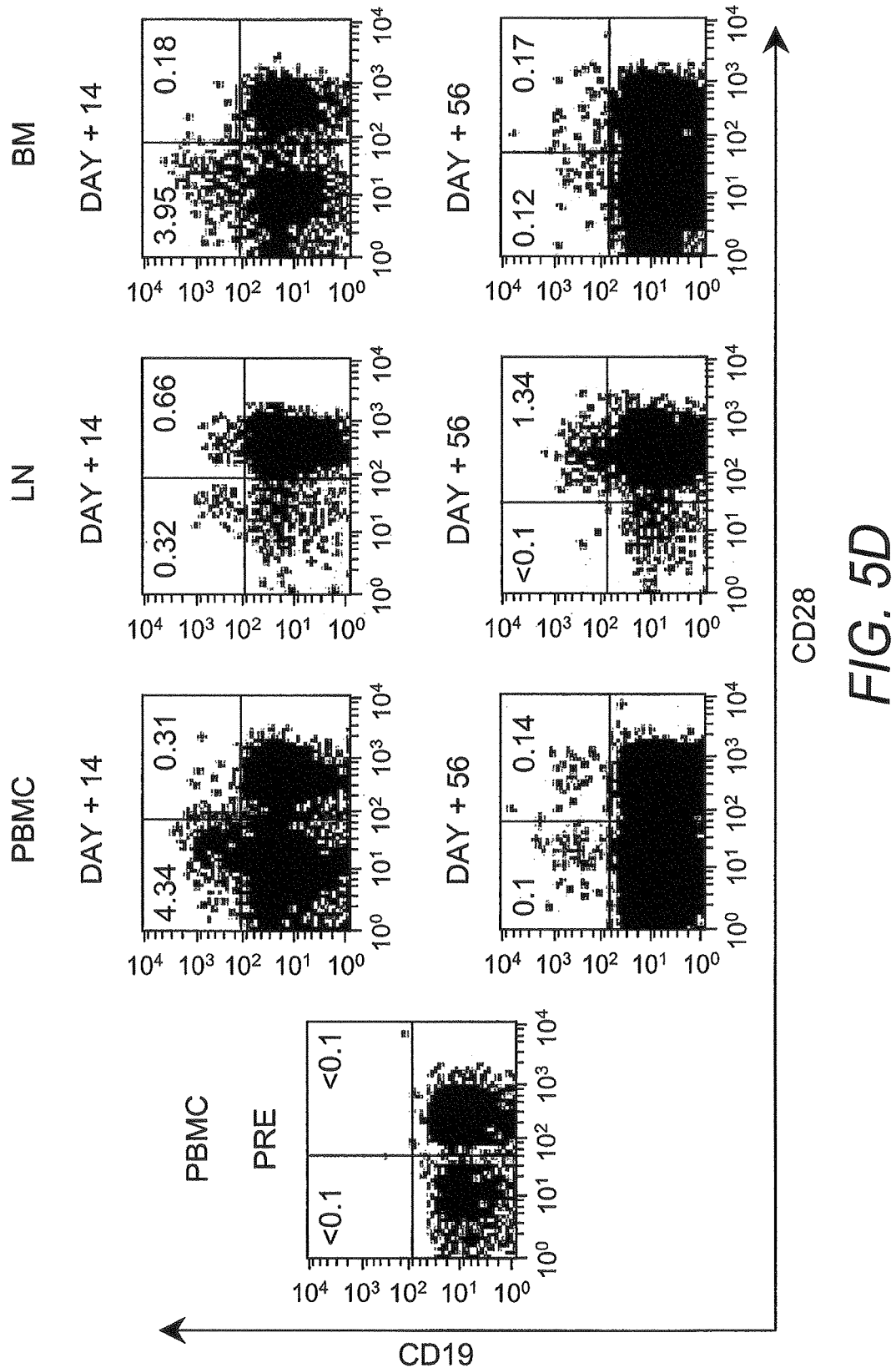
Figure 5E:
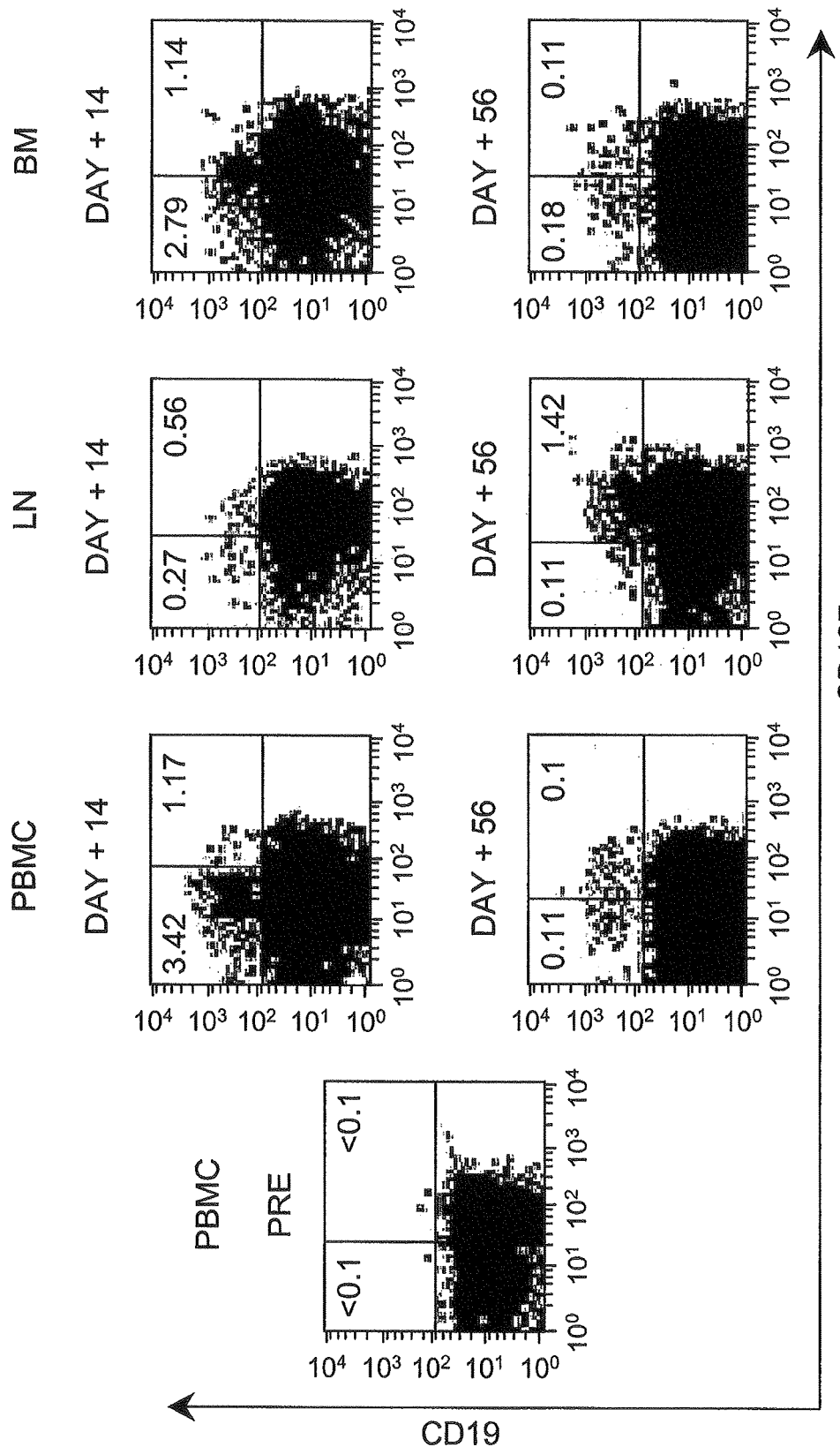

CD62L was not expressed during the brief period the $T_{EM}$-derived clone persisted in the blood in any of the three macaques (FIG. 5a). We next examined whether the T cells that persisted in vivo after adoptive transfer acquired other phenotypic markers of memory T cells that were absent on the infused $T_E$. Fourteen days after cell transfer, a subset of the CD19$^+$CD8$^+$ T cells in blood and lymph node expressed CCR7, CD28, and CD127 (FIGS. 5c-e). We repeated this analysis on blood, bone marrow, and lymph node samples obtained two months after the infusion of the $T_{CM}$-derived clone in macaque 02258. At this later time, the infused CD19$^+$ T cells comprised 1.4% of the CD8$^+$ T cells in the lymph node and these T cells were uniformly positive for $T_{CM}$ markers including CD62L, CCR7, CD28, and CD 127 (FIGS. 5b-e). Transferred T cells were present at lower levels in the blood and bone marrow, and contained both CD62L$^+$ and CD62L$^-$ fractions. The transferred CD19$^+$ T cells that persisted long-term in the blood and expressed CD62L, also expressed CR7, CD28 and CD127 (not shown). Thus, despite differentiation to $T_E$ during expansion of a single $T_{CM}$ cell to more than 5×10$^9$ cells, a significant fraction of the transferred T cell clones were able to persist long-term, compete with endogenous T cells for anatomical niches of $T_{CM}$, and re-express phenotypic markers of $T_{CM}$.

Memory T Cells Established by Adoptive Transfer Exhibit Functional Properties of Both $T_{CM}$ and $T_{EM}$.

An objective of T cell immunotherapy is to establish a stable pool of memory T cells that can respond to antigen by producing cytokines and differentiating into cytolytic effector cells. The transferred CD19$^+$ $T_{CM}$-derived cells that persisted in the blood produced IFN-γ after peptide stimulation and their frequency was comparable to endogenous CD 19$^-$ CMV-specific CD8$^+$ T cells (FIG. 6a). The cytolytic function of these T cells was examined by sorting T cells from the blood into CD19$^+$CD62L$^+$CD8$^+$ and CD19$^+$CD62L$^-$CD8$^+$ fractions. For these experiments, it was necessary to pool PBMC samples from multiple time points to obtain sufficient cells for the assays. The CD19$^+$CD62L$^-$ T cells demonstrated cytolytic activity nearly equivalent to that of the T cell clone and expressed granzyme B, while the CD19$^+$CD62L$^+$ T cells lacked direct cytolytic activity and had low granzyme B expression (FIG. 6b). In vitro stimulation of the CD 19$^+$CD62L$^+$ T cells with anti-CD3 and anti-CD28 monoclonal antibodies generated $T_E$ cells with cytolytic activity, demonstrating these cells could be re-induced to differentiate to cytolytic $T_E$ (FIG. 6b). We also labeled the sorted CD19$^+$CD62L$^+$ and CD19$^+$CD62L$^-$ T cell fractions with CFSE and monitored proliferation five days after antigen stimulation in vitro. Seventy-four percent of CD62L$^+$ cells underwent 5 or more cell divisions, but only 13% of CD62L$^-$ cells underwent 5 or more divisions (FIG. 6c). Thus, the adoptive transfer of a $T_E$ clone derived from the $T_{CM}$ pool established distinct populations of cells in vivo with the functional properties of $T_{CM}$ and $T_{EM}$.

We have previously shown in human studies that the infusion of T cells that express a foreign antigen can prime and boost endogenous antigen-specific memory T cell responses[31]. Thus, to determine if $T_M$ established by adoptive transfer could respond to antigen stimulation in vivo, we infused a small dose (1×10$^7$/kg) of autologous T cells pulsed with CMV IE peptide (T-APC) into macaque A99171 two months after administering the ΔCD19-modified $T_{CM}$-derived T cells. The peptide pulsed T-APC were efficiently lysed by the CMV-specific T cell clone in vitro (FIG. 6e). Within 7 days of the infusion of T-APC, there was a 4 to 5-fold increase in the absolute numbers of both ΔCD19-modified and endogenous IE-specific T cells in the blood (FIG. 6d). Thus, the memory T cells established by adoptive transfer were as capable as endogenous memory T cells of expanding in response to antigen in vivo.

Discussion

Poor survival of adoptively transferred T cells that target infected or cancerous cells has correlated with lack of therapeutic efficacy in clinical trials[14,16,16]. The persistence and efficacy of cultured T cells can sometimes be improved by depletion of host lymphocytes prior to cell transfer to eliminate regulatory cells and competition for pro-survival cytokines, and by the administration of IL-2 after cell transfer[16,17]. However, these interventions are not uniformly successful in improving cell persistence suggesting that intrinsic properties of T cells isolated for adoptive therapy may be critical for establishing durable immunity. Here, we used gene marking to show that antigen-specific CD8$^+$ $T_E$ clones derived in vitro from the $T_{CM}$ but not from the $T_{EM}$ subset, persist longterm in vivo, occupy memory T cell niches, and reacquire phenotypic and functional properties of $T_{CM}$ after adoptive transfer.

After encountering antigen in vivo, T cells undergo proliferation and programmed differentiation evoked by signals from the TCR, co-stimulatory and adhesion molecules, and cytokine receptors[18,20,32]. These events result in the generation of large numbers of $T_E$ that die as antigen is cleared, and a smaller pool of phenotypically distinct $T_{CM}$ and $T_{EM}$ that persist for life and respond to antigen re-exposure by differentiating into $T_E$. Data from both murine and human studies support a linear differentiation model in which $T_{CM}$ give rise to both $T_{EM}$ and $T_E$, although it remains possible that $T_{CM}$ and $T_{EM}$ represent separate lineages[18,33-35]. The capacity of T cell memory to be maintained for life suggests that at least some $T_M$ must be capable of both self-renewal and differentiation[23].

The results presented here suggest that isolating $T_{CM}$ for gene insertion may provide a tumor-reactive T cell population with an improved capacity to persist after adoptive transfer.

REFERENCES

1. Cheever, M. A., et al., Specificity of adoptive chemoimmunotherapy of established syngeneic tumors. *J. Immunol.* 125, 711-714 (1980).
2. Pahl-Seibert, M.-F. et al. Highly protective in vivo function of cytomegalovirus IE1 epitope-specific memory CD8 T cells purified by T-cell receptor-based cell sorting. *J. Virol.* 79, 5400-5413 (2005).

3. Riddell, S. R. et al. Restoration of viral immunity in immunodeficient humans by the adoptive transfer of T cell clones. *Science* 257, 238-241 (1992).
4. Walter, E. A. et al. Reconstitution of cellular immunity against cytomegalovirus in recipients of allogeneic bone marrow by transfer of T-cell clones from the donor. *N. Engl. J. Med.* 333, 1038-1044 (1995).
5. Rooney, C. M. et al. Infusion of cytotoxic T cells for the prevention and treatment of Epstein-Barr virus-induced lymphoma in allogeneic transplant recipients. *Blood* 92, 1549-1555 (1998).
6. Dudley, M. E. et al. Cancer regression and autoimmunity in patients after clonal repopulation with antitumor lymphocytes. *Science* 298, 850-854 (2002).
7. Bollard, C. M. et al. Cytotoxic T lymphocyte therapy for Epstein-Barr virus+ Hodgkin's disease. *J. Exp. Med.* 200, 1623-1633 (2004).
8. Dudley, M. E. et al. Adoptive cell transfer therapy following nonmyeloablative but lymphodepleting chemotherapy for the treatment of patients with refractory metastatic melanoma. *J. Clin. Oncol.* 23, 2346-2357 (2005).
9. Gattinoni, L., Powell Jr, D. J., Rosenberg, S. A., & Restifo, N. P. Adoptive immunotherapy for cancer: building on success. *Nat. Rev. Immunol.* 6, 383-393 (2006).
10. Blattman, J. N. & Greenberg, P. D. Cancer Immunotherapy: A treatment for the masses. *Science* 305, 200-205 (2004).
11. Kessels, H. W. H. G. et al. Immunotherapy through TCR gene transfer. *Nat. Immunol.* 2, 957-961 (2001).
12. Stanislawski, T. et al. Circumventing tolerance to a human MDM2-derived tumor antigen by TCR gene transfer. *Nat. Immunol.* 2, 962-970 (2001).
13. Brentjens, R. J. et al. Eradication of systemic B-cell tumors by genetically targeted human T lymphocytes co-stimulated by CD80 and interleukin-15. *Nat. Med.* 9, 279-286 (2003).
14. Morgan, R. A. et al. Cancer regression in patients after transfer of genetically engineered lymphocytes. *Science* advance online publication Aug. 31, (2006). DOI: 10.1126/science.1129003
15. Blcakley, M. & Riddell, S. R. Molecules and mechanisms of the graftversus-leukemia effect. *Nat. Rev. Cancer* 4, 371-380 (2004).
16. Dudley, M. E. et al. Adoptive transfer of cloned melanoma-reactive T lymphocytes for the treatment of patients with metastatic melanoma. *J. Immunother.* 24, 363-373 (2001).
17. Yee, C. et al. Adoptive T cell therapy using antigen-specific CD8+ T cell clones for the treatment of patients with metastatic melanoma: In vivo persistence, migration, and antitumor effect of transferred cells. *Proc. Natl. Acad. Sci. USA* 99, 16168-16173 (2002).
18. Sallusto, F. et al., Central memory and effector memory T cell subsets: function, generation, and maintenance. *Annu. Rev. Immunol.* 22, 745-763 (2004).
19. Butcher, E. C. & Picker, L. J. Lymphocyte homing and homeostasis. *Science* 272, 60-66 (1996).
20. Wherry, E. J. et al. Lineage relationship and protective immunity of memory CD8 T cell subsets. *Nat. Immunol.* 4, 225-234 (2003).
21. Dudley, M. E. et al. A phase I study of nonmyeloablative chemotherapy and adoptive transfer of autologous tumor antigen-specific T lymphocytes in patients with metastatic melanoma. *J. Immunother.* 25, 243-251 (2002).
22. Gattinoni, L. et al. Acquisition of full effector function in vitro paradoxically impairs the in vivo antitumor efficacy of adoptively transferred CD8+ T cells. *J. Clin. Invest.* 115, 1616-1626 (2005).
23. Fearon, D. T. et al., Arrested differentiation, the self-renewing memory lymphocyte, and vaccination. *Science* 293, 248-250 (2001).
24. Zhang, Y. et al. Host-reactive CD8+ memory stem cells in graft-versus host disease. *Nat. Med.* 11, 1299-1305 (2005).
25. Pitcher, C. J. et al. Development and homeostasis of T cell memory in rhesus macaque. *J. Immunol.* 168, 29-43 (2002).
26. Sopper, S. et al. Impact of simian immunodeficiency virus (SIV) infection on lymphocyte numbers and T-cell turnover in different organs of rhesus monkeys. *Blood* 101, 1213-1219 (2003).
27. Venues, I. et al., A novel assay for apoptosis. Flow cytometric detection of phosphatidylserine expression on early apoptotic cells using fluorescein labelled Annexin V. *J. Immunol. Methods* 184, 39-51 (1995).
28. Schluns, K. S. et al. Requirement for IL-15 in the generation of primary and memory antigen-specific CD8 T cells. *J. Immunol.* 168, 4827-4831 (2002).
29. Becker, T. C. et al. Interleukin 15 is required for proliferative renewal of virus-specific memory CD8 T cells. *J. Exp. Med.* 195, 1541-1548 (2002).
30. Marks-Konczalik, J. et al. IL-2-induced activation-induced cell death is inhibited in IL-15 transgenic mice. *Proc. Natl. Acad. Sci. USA* 97, 11445-11450 (2000).
31. Berger, C. et al., Analysis of transgene-specific immune responses that limit the in vivo persistence of adoptively transferred HSV-TK-modified donor T cells after allogeneic hematopoietic cell transplantation. *Blood* 107, 2294-2302 (2006).
32. Masopust, D. et al., The role of programming in memory T-cell development. *Curr. Opin. Immunol.* 16, 217-225 (2004).
33. Appay, V. et al. Memory CD8+ T cells vary in differentiation phenotype in different persistent virus infections. *Nat. Med.* 8, 379-385 (2002).
34. Marzo, A. L. et al. Initial T cell frequency dictates memory CD8+ T cell lineage commitment. *Nat. Immunol.* 6, 793-799 (2005).
35. Lefrançois, L. & Marzo, A. The descent of memory T-cell subsets. *Nat. Rev. Immunol.* 6, 618-623 (2006).
36. Kaech, S. M. et al. Selective expression of the interleukin 7 receptor identifies effector CD8 T cells that give rise to long-lived memory cells. *Nat. Immunol.* 4, 1191-1198 (2003).
37. Willinger, T. et al. Molecular signatures distinguish human central memory from effector memory CD8 T cell subsets. *J. Immunol.* 175, 5895-5903 (2005).
38. Wilson, C. B. & Merkenschlager, M. Chromatin structure and gene regulation in T cell development and function. *Curr. Opin. Immunol.* 18, 143-151 (2006).
39. Klebanoff, C. A. et al. Central memory self/tumor-reactive CD8+ T cells confer superior antitumor immunity compared with effector memory T cells. Proc. Natl. Acad. Sci. USA 102, 9571-9576 (2005).
40. Lee, P. P. et al. Characterization of circulating T cells specific for tumorassociated antigens in melanoma patients. *Nat. Med.* 5, 677-685 (1999).
41. Groh, V., Wu, J., Yee, C., & Spies, T. Tumour-derived soluble MIC ligands impair expression of NKG2D and T-cell activation. *Nature* 419, 734-738 (2002).
42. Sadelain, M., Riviere, I., & Brentjens, R. J. Targeting tumours with genetically enhanced T lymphocytes. *Nat. Rev. Cancer* 3, 35-45 (2003).

43. Engels, B. et al. Retroviral vectors for high-level transgene expression in T lymphocytes. *Hum. Gene Ther.* 14, 1155-1168 (2003).
44. Riddell, S. R. et al. T-cell mediated rejection of gene-modified HIV specific cytotoxic T lymphocytes in HIV-infected patients. *Nat. Med.* 2, 216-223 (1996).
45. Berger, C. et al. Nonmyeloablative immunosuppressive regimen prolongs in vivo persistence of gene-modified autologous T cells in a nonhuman primate model. *J. Virol.* 75, 799-808 (2001).
46. Barratt-Boyes, S. M. et al. Maturation and trafficking of monocyte derived dendritic cells in monkeys: implications for dendritic cell-based vaccines. *J. Immunol.* 164, 2487-2495 (2000).
47. Berger, C. et al. Pharmacologically regulated Fas-mediated death of adoptively transferred T cells in a nonhuman primate model. *Blood* 103, 1261-1269 (2004).
48. Heid, C. A., Stevens, J., Livak, K. J., & Williams, P. M. Real time quantitative PCR. *Genome Res.* 6, 986-994 (1996).
49. Rufer, N. et al. Telomere length dynamics in human lymphocyte subpopulations measured by flow cytometry. *Nat. Biotechnol.* 16, 743-747 (1998).
50. Baerlecher, G. M. & Lansdorp, P. M. Telomere length measurements in leukocyte subsets by automated multicolor flow-FISH. Cytometry A 55A, 1-6 (2003).

The foregoing is illustrative of the present invention, and is not to be construed as limiting thereof. The invention is defined by the following claims, with equivalents of the claims to be included therein.

The invention claimed is:

1. A cytotoxic T lymphocyte (CTL) preparation, wherein the CTL preparation comprises 60% or more primate CD8+ effector T ($T_E$) cells and one or more of the CD8+$T_E$ cells of the CTL preparation comprise a gene encoding a protein that specifically binds to a target on a cell, wherein the 60% or more primate CD8+$T_E$ cells have: (a) decreased expression of CD62L as compared to CD8+ central memory T ($T_{CM}$) cells; and (b) improved survival and/or expansion for at least 10 days when cultured in vitro in the presence of IL-15 and in the absence of antigen stimulation as compared to when cultured in vitro in the absence of IL-15 and in the absence of antigen stimulation.

2. The CTL preparation according to claim 1, wherein the CD8+$T_E$ cells of the CTL preparation are positive for granzyme B, perforin or both.

3. The CTL preparation according to claim 1, wherein the CD8+$T_E$ cells of the CTL preparation have decreased expression of CCR7, CD28, and CD127 as compared to CD8+$T_{CM}$ cells.

4. The CTL preparation according to claim 2, wherein the 60% or more of CD8+$T_E$ cells of the CTL preparation have improved survival and/or expansion in vitro for at least 34 days in the presence of IL-15.

5. The CTL preparation according to claim 1, wherein the CD8+$T_E$ cells of the CTL preparation persist in vivo upon adoptive transfer to a primate subject for at least 5 days, at least 7 days, at least 10 days, at least 14 days, at least 21 days, at least 28 days, at least 42 days, at least 56 days, at least 70 days, at least 77 days, at least 215 days, or at least 344 days.

6. The CTL preparation according to claim 1, wherein the gene encoding a protein that specifically binds to the target on the cell is an engineered immunoreceptor.

7. The CTL preparation according to claim 6, wherein the target is on a cancer cell.

8. The CTL preparation according to claim 7, wherein the cancer cell target is CD19 or CD20.

9. The CTL preparation according to claim 1, wherein the primate is a human.

10. The CTL preparation according to claim 1, wherein the CTL preparation comprises 70%, 80%, 85% or 90% or more of the primate CD8+$T_E$ cells having the decreased expression of CD62L.

11. The CTL preparation according to claim 1, wherein the CTL preparation consists essentially of the primate CD8+$T_E$ cells having the decreased expression of CD62L.

12. The CTL preparation according to claim 1, further comprising IL-15.

13. The CTL preparation according to claim 1, wherein the CTL preparation is formulated in a pharmaceutically acceptable carrier.

14. A method for producing a CD8+ cytotoxic T lymphocyte (CTL) preparation useful for adoptive immunotherapy, comprising the steps of:
   (a) enriching a subpopulation of CD62L+CD8+ central memory T ($T_{CM}$) lymphocytes from a T lymphocyte population from a primate subject;
   (b) introducing, into cells of the $T_{CM}$-enriched subpopulation, a gene encoding a protein that specifically binds to a target on a cell; and
   (c) expanding the $T_{CM}$-enriched subpopulation in vitro to produce a CD8+ CTL preparation comprising a majority of CD8+ effector T ($T_E$) cells having decreased expression of CD62L as compared to the CD8+ $T_{CM}$-enriched subpopulation before expansion, wherein cells of the CD8+ CTL preparation having decreased expression of CD62L will have improved survival and/or expansion for at least 10 days when cultured in vitro in the presence of IL-15 and in the absence of antigen stimulation as compared to when cultured in vitro in the absence of IL-15 and in the absence of antigen stimulation.

15. The method according to claim 14, wherein the $T_{CM}$-enriched subpopulation further comprises expansion in vitro in the presence of IL-15.

16. A CD8+ cytotoxic T lymphocyte (CTL) preparation, prepared by the method of claim 14, wherein the cells of the CTL preparation having decreased expression of CD62L as compared to the CD8+ $T_{CM}$-enriched subpopulation before expansion will have improved survival and/or expansion for at least 10 days when cultured in vitro in the presence of IL-15 and absence of antigen stimulation as compared to when cultured in vitro in the absence of IL-15 and in the absence of antigen stimulation.

* * * * *

UNITED STATES PATENT AND TRADEMARK OFFICE
CERTIFICATE OF CORRECTION

PATENT NO. : 10,400,215 B2
APPLICATION NO. : 14/303385
DATED : September 3, 2019
INVENTOR(S) : Stanley R. Riddell et al.

It is certified that error appears in the above-identified patent and that said Letters Patent is hereby corrected as shown below:

On the Title Page

Item (73) Assignees:
"(73) Assignees: City of Home, Duarte, CA (US); Fred Hutchinson Cancer Research Center, Seattle, WA (US)"

Should read:
--(73) Assignees: City of Hope, Duarte, CA (US); Fred Hutchinson Cancer Research Center, Seattle, WA (US)--.

Signed and Sealed this
Tenth Day of September, 2024

Katherine Kelly Vidal
*Director of the United States Patent and Trademark Office*